United States Patent
Bouchard et al.

(10) Patent No.: US 8,502,180 B2
(45) Date of Patent: Aug. 6, 2013

(54) APPARATUS AND METHOD HAVING DUAL SENSOR UNIT WITH FIRST AND SECOND SENSING FIELDS CROSSED ONE ANOTHER FOR SCANNING THE SURFACE OF A MOVING ARTICLE

(75) Inventors: Michel R. Bouchard, St-Augustin-de-Desmaures (CA); Yvon Legros, Québec (CA); Jean-Yves Garneau, Saint-Jean-Chrysostôme (CA); Guy Dion, Québec (CA)

(73) Assignee: Centre de Recherche Industrielle du Quebec, Quebec (CA)

( * ) Notice: Subject to any disclaimer, the term of this patent is extended or adjusted under 35 U.S.C. 154(b) by 864 days.

(21) Appl. No.: 12/693,693

(22) Filed: Jan. 26, 2010

(65) Prior Publication Data
US 2010/0188500 A1    Jul. 29, 2010

Related U.S. Application Data

(63) Continuation-in-part of application No. 12/359,382, filed on Jan. 26, 2009, now Pat. No. 8,193,481.

(51) Int. Cl.
*G01N 21/86*    (2006.01)
(52) U.S. Cl.
USPC ................................. 250/559.4; 250/223 R
(58) Field of Classification Search
USPC .................. 250/559.4, 221, 223 R, 239, 216, 250/234–236, 208.1, 559.22; 356/372–376, 356/237.1–237.5, 399–401
See application file for complete search history.

(56) References Cited

U.S. PATENT DOCUMENTS

| | | | |
|---|---|---|---|
| 3,942,021 A | | 3/1976 | Barr et al. |
| 3,983,403 A | | 9/1976 | Dahlstrom |
| 4,221,974 A | | 9/1980 | Mueller |
| 4,286,880 A | | 9/1981 | Young |
| 4,301,373 A | | 11/1981 | Sjodin |
| 4,392,204 A | | 7/1983 | Prim et al. |
| 4,500,203 A | | 2/1985 | Bieringer |
| 4,691,365 A | | 9/1987 | Nagashima |
| 4,803,371 A | | 2/1989 | Durland |
| 5,254,859 A | | 10/1993 | Carman et al. |
| 5,544,757 A | | 8/1996 | Geiger et al. |
| 5,644,392 A | | 7/1997 | Soest et al. |
| 5,949,086 A | | 9/1999 | Reponen et al. |
| 5,960,104 A | | 9/1999 | Conners et al. |
| 6,122,065 A | | 9/2000 | Gauthier |
| 6,166,393 A | * | 12/2000 | Paul et al. ............... 250/559.08 |
| 6,199,463 B1 | | 3/2001 | Quick |
| 6,272,437 B1 | | 8/2001 | Woods et al. |
| 6,366,351 B1 | | 4/2002 | Ethier et al. |
| 6,466,305 B1 | | 10/2002 | McBain |

(Continued)

*Primary Examiner* — Que T Le
(74) *Attorney, Agent, or Firm* — Jean-Claude Boudreau

(57) ABSTRACT

An apparatus and method for scanning a surface of an article moving along a travel path axis provide a compact sensor configuration. A first sensor unit has a first sensing field transversely directed toward the travel path axis and defining a first scanning zone. A second sensor unit has a second sensing field transversely directed toward the travel path axis and defining a second scanning zone. The first and second sensing fields are crossing one with another at a location sufficiently remote from the first and second scanning zones so as to not adversely affect the generation of sensor output data, while providing a compact arrangement of sensor units.

29 Claims, 16 Drawing Sheets

U.S. PATENT DOCUMENTS

| | | |
|---|---|---|
| 6,690,990 B1 | 2/2004 | Caron et al. |
| 6,708,122 B2 | 3/2004 | Lessard et al. |
| 6,750,466 B2 | 6/2004 | Guha et al. |
| 6,956,963 B2 | 10/2005 | Ulrich et al. |
| 7,047,153 B2 | 5/2006 | Woods et al. |
| 7,215,363 B2 | 5/2007 | Stamm |
| 7,429,999 B2 | 9/2008 | Poulin et al. |
| 2003/0009894 A1 | 1/2003 | Yamamoto |
| 2004/0025654 A1 | 2/2004 | Olson |
| 2004/0246473 A1 | 12/2004 | Hermary et al. |
| 2005/0120840 A1 | 6/2005 | Koskovish |
| 2007/0034297 A1 | 2/2007 | Zielke |
| 2007/0263918 A1 | 11/2007 | Jenya |

\* cited by examiner

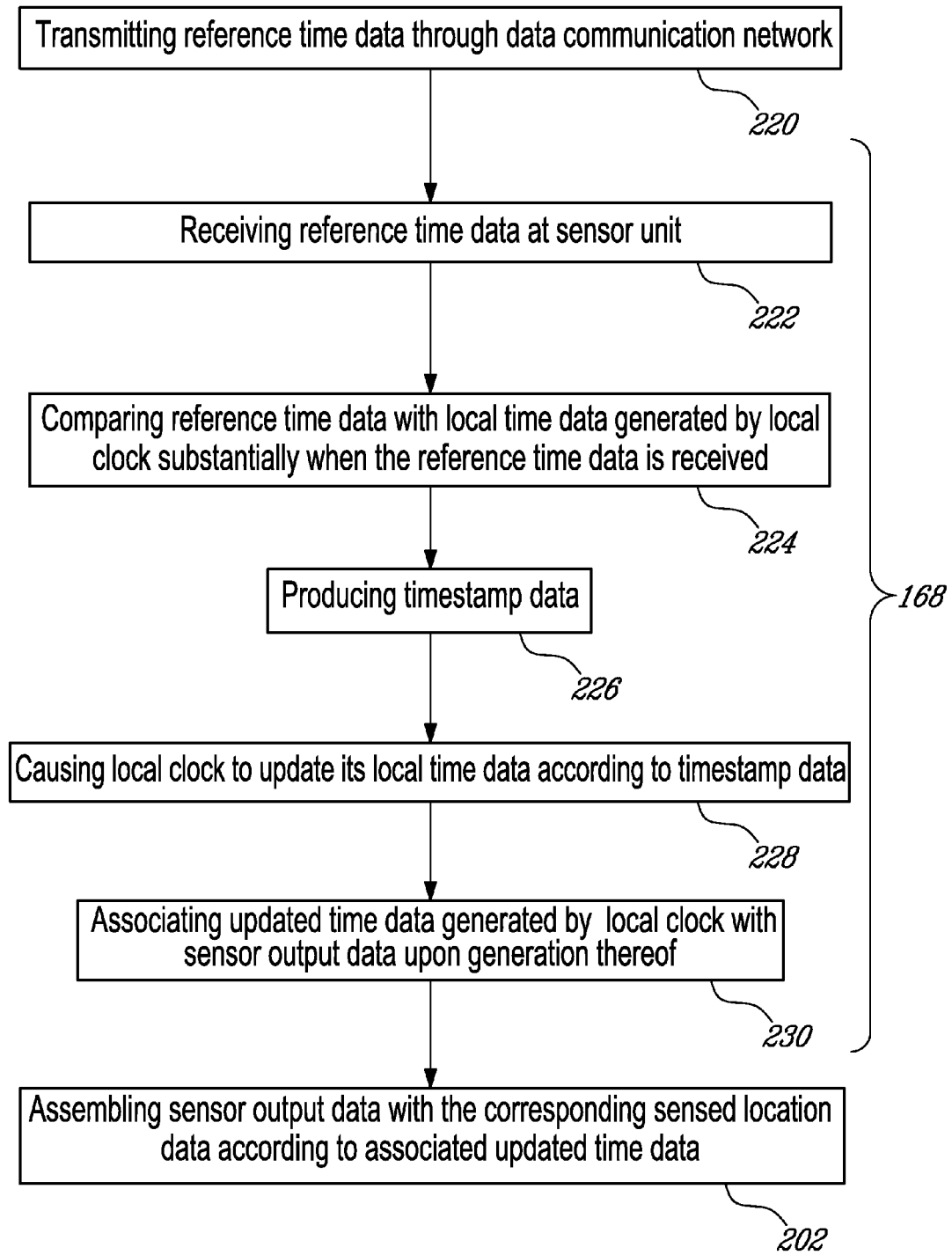

APPARATUS AND METHOD HAVING DUAL SENSOR UNIT WITH FIRST AND SECOND SENSING FIELDS CROSSED ONE ANOTHER FOR SCANNING THE SURFACE OF A MOVING ARTICLE

REFERENCE TO PRIOR APPLICATION

This application is a continuation-in-part of co-pending U.S. patent application Ser. No. 12/359,398 entitled "Method and Apparatus for Assembling Sensor Output Data with Sensed Location Data" filed Jan. 26, 2009.

FIELD OF THE INVENTION

The present invention relates to the field of computerized instrumentation and more particularly to apparatus and methods for scanning the surface of moving articles.

BACKGROUND OF THE INVENTION

During the past years, systems for scanning the surface of moving articles have been developed and applied for grading or quality control purposes in many high volume manufacturing applications such as found in the automotive, consumer electronics, agricultural, food or lumber processing industries. In some applications, many characteristics of the articles must be detected, thus requiring integration of several scanning sensors of different types such as optical, ultrasonic and X-rays sensors, whose outputs are combined for the desired purpose. A typical configuration of sensors integrated in a sensor subsystem as part of a wooden board processing system is schematically shown in FIG. 1d. The sensor subsystem includes a first optical sensor unit provided with a first camera 2 having a first sensing field 3 defining a first scanning zone 4, to generate first sensor output data related to surface of board 16 as scanned by a laser 5 while moving in the direction of arrow 18. The sensor subsystem further includes a second optical sensor unit provided with a second camera 6 having a second sensing field 7 defining a second scanning zone 8, to generate second sensor output data related to the scanned board surface as illuminated by light source 9. It can be appreciated that the sensor subsystem according to the prior art configuration shown in FIG. 1d exhibits an increased overall dimension $L_2$ as a result of the integration of two sensor units, as compared to the dimension $L_1$ exhibited by single first sensor unit. An example of such known optical scanning subsystem integrating a plurality of sensors is disclosed in U.S. Pat. No. 5,960,104 to Conners et al.

BRIEF DESCRIPTION OF THE DRAWINGS

Various embodiments of the invention will be described with reference to the accompanying drawings in which:

FIG. 1b is a perspective view of the profile and image sensor units as part of the sensor subsystem shown in FIG. 1a;

FIG. 8 is a flow chart showing the main steps used by data assembling methods that can be implemented in the optimization system of FIG. 1;

SUMMARY OF INVENTION

According to a broad aspect of the invention, there is provided an apparatus for scanning at least one surface of an article moving along a travel path axis, comprising a profile sensor unit having a first sensing field transversely directed toward the travel path axis and defining a first scanning zone, to generate profile-related sensor output data related to the article surface, and a color image sensor unit having a second sensing field transversely directed toward the travel path axis and defining a second scanning zone, to generate color-related sensor output data related to the article surface. The first and second sensing fields are crossing one with another at a location sufficiently remote from the first and second scanning zone so as to not adversely affect the generation of the profile-related and color-related sensor output data, while providing a compact arrangement of the profile and color image sensor units.

According to another broad aspect of the invention, there is provided a method for scanning at least one surface of an article moving along a travel path axis, comprising: i) transversely directing a first sensing field of a profile sensor unit toward the travel path axis, the first sensing field defining a first scanning zone, to generate profile-related sensor output data related to the article surface; and ii) transversely directing a second sensing field of a color image sensor unit toward the travel path axis, the second sensing field defining a second scanning zone, to generate color-related sensor output data related to the article surface;

wherein said first and second sensing fields are crossing one with another at a location sufficiently remote from the first and second scanning zone so as to not adversely affect the generation of the profile-related and color-related sensor output data, while providing a compact arrangement of the profile and color image sensor units.

DETAILED DESCRIPTION OF THE EMBODIMENTS

Figure 1:
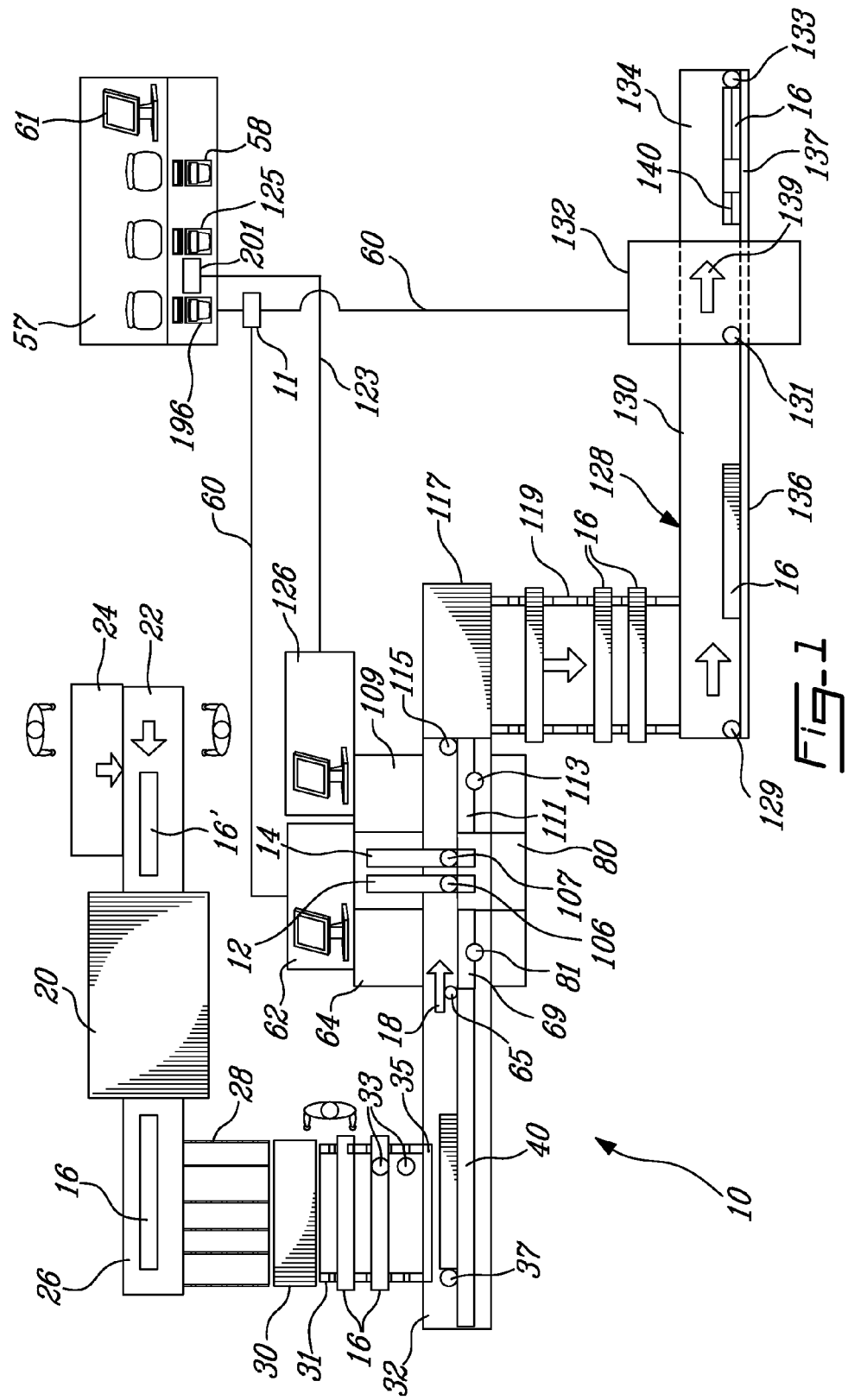
FIG. 1 is a schematic representation of a wooden board cutting optimization system as an implementation example of the surface scanning apparatus and as herein described.

In the context of an application example that will be discussed in view of FIG. 1, various embodiments of apparatus and methods for scanning at least one surface of an article moving along a travel path axis will now be described. FIG. 1 schematically shows the main components of a wooden board optimization system generally designated at 10, which provides a cutting solution into subdivided products from each board 16 according to a predetermined cutting bill, providing an optimum yield in term of either economic value or material utilization. A two-axis optimization approach as implemented in the system 10 is described in U.S. Pat. No. 6,690,990 issued to the same assignee as of the present invention, the content thereof being incorporated herein by reference.

The exemplary system 10 may be used by a furniture manufacturing plant to increase production yields by upgrading wooden parts produced with respect to raw wooden board quality and by minimizing the impact of any raw wood quality decrease upon profitability and performance of the furniture manufacturing plant. The optimization approach used by system 10 is based on automatic board defect detection in combination with a two-axis optimization approach to provide an optimal board cutting plan. The system 10 is particularly adapted to receive boards 16 from a planer 20 capable of machining rough top and bottom surfaces of a raw wooden board 16' coming from infeed conveyor 22 from board loading station 24. Adjacent an outfeed conveyor 26 receiving surfaced boards 16 is a transfer chain conveyor 28 that discharges each board to a loader 30 from which individualized board 16 are in turn discharged to a catching chain conveyor 31 adjacent to which are disposed photoelectric cells 33 connected through communication network 11 to a control unit 58 such as a programmable logic controller (PLC) as part of a control centre 57 also including a system main control module 196 and a part production management station at 61, the functions of which will be described later in detail. The cells 33 generate signals to PLC 58 when leading edge and trailing edge of a board successively pass through respective sensing fields of cells 33 to provide an indication of board width. Disposed at an output end of conveyor 31 is a discharging device 35 provided with a controllable ramp allowing discharge of individualized boards one after another on a system entry conveyor 32 upon command signals from PLC 58. The conveyor 32 is provided with a photoelectric cell 37 used to detect a board 16 coming from discharging device 35 and to indicate accordingly to PLC 58 that an appropriate command for an adjustable fence provided on a guiding device 40 can be sent according to board width that has been previously measured using photoelectric cells 33. The system entry conveyor 32 receives command signals from PLC 58 through a communication line provided on network bus 60 via local control/monitoring station 62 linked to data communication network 11. The PLC 58 is programmed to provide regulation of board feeding into the system 10 through the operation of conveyor 32. The local control/monitoring station 62 is also programmed to allow manual operation of discharging device 35, conveyor 32, and guiding device 40 as desired by an operator.

Still in view of FIG. 1, disposed adjacent a forward end of system entry conveyor 32 is a sensor subsystem entry conveyor 64 designed to provide board stability and to regulate its feeding speed at a predetermined value, under the command of PLC 58. At entry conveyor 64 there is provided a photoelectric cell 65 to indicate through a corresponding electrical signal when the leading edge and trailing edge of a processed board sequentially enter the sensor subsystem 80. The location of photoelectric cell 65 corresponds to the position of a sensor subsystem reference point that can be considered for the purpose of data assembling, as will be explained later in detail. The conveyor 64 is of a similar design than system entry conveyor 32, and is also governed by PLC 58 through control/monitoring station 62. The conveyor 64 has an adjustable fence 69 for providing board width adaptation through the operation of displaceable actuators (not shown). The transverse position of fence 69 is adjusted according to the previously made width measurement of the conveyed board to provide alignment thereof along a travel path axis 44 in a feeding direction indicated by arrow 18. The adjustable fence 69 is associated with a photoelectric cell 81 indicating to the PLC 58 that it reaches its target position. Here again, the local control/monitoring station 62 is programmed to selectively provide a manual operation of all main components of the sensor subsystem entry conveyor 64.

Figure 1A:
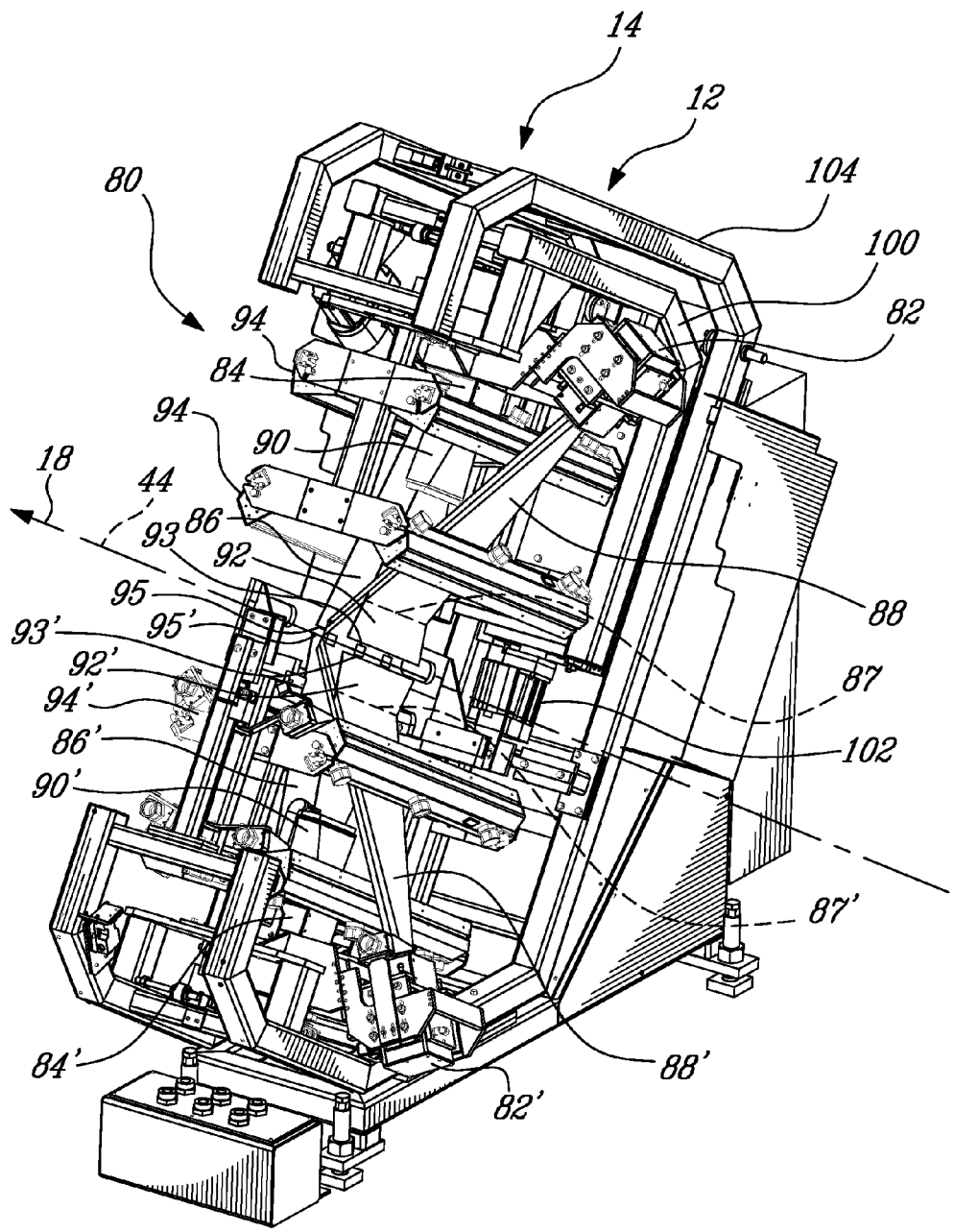
FIG. 1a is a perspective view of a sensor subsystem as part of a board cutting optimization system such as schematically shown in FIG. 1.
Figure 1B:
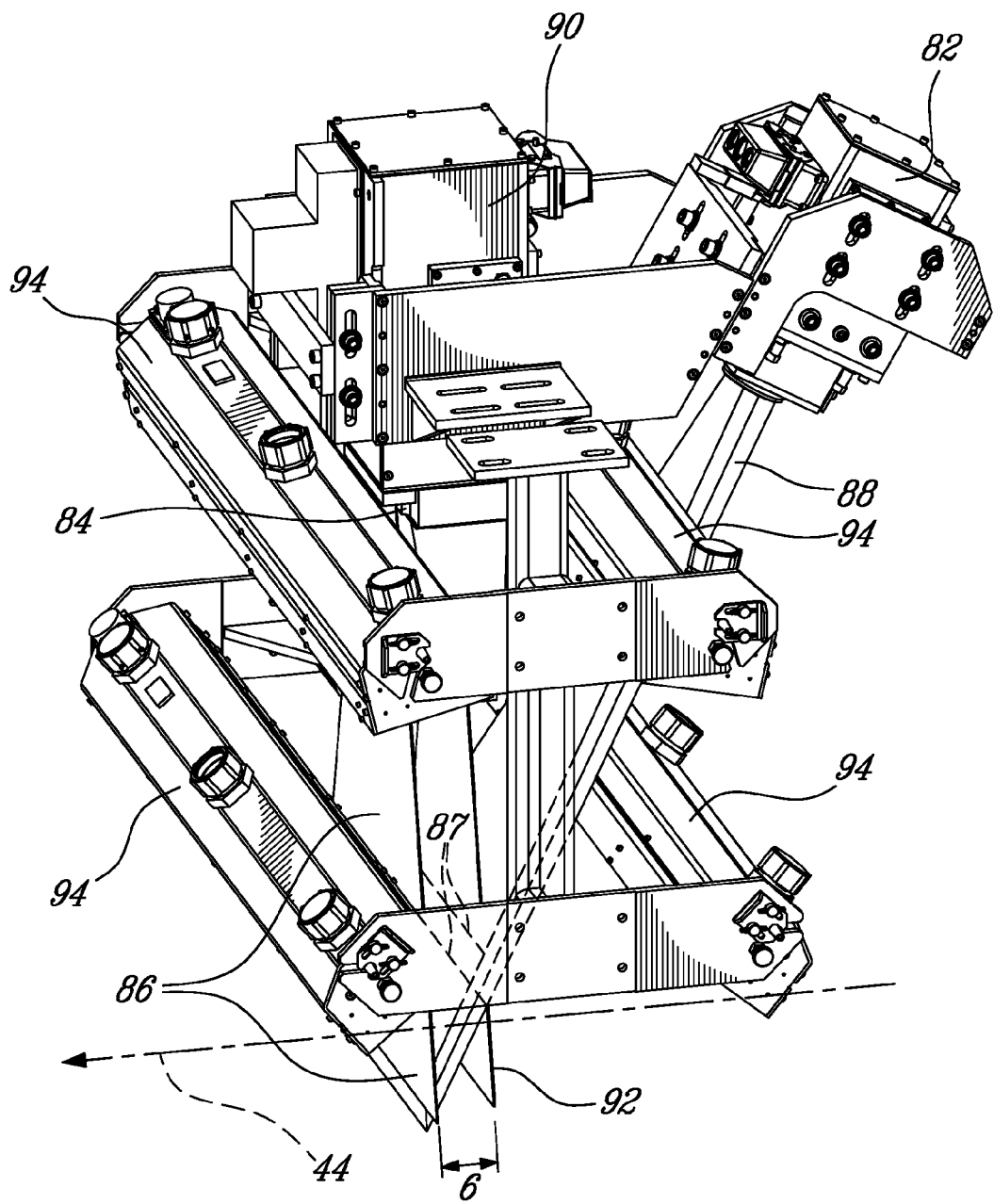

The system 10 further includes a sensor subsystem located downstream conveyor 64 and generally designated at 80 as shown in FIGS. 1a and 1b, which includes a first sensor unit 12 having a first sensing field 88 transversely directed toward travel path axis 44 and defining a first scanning zone 95, to generate first sensor output data related to the scanned board surface. In the presently described embodiment, the sensor unit 12 is an optical, profile sensor unit, the generated first sensor output data representing profile-related characteristics of the scanned surface. The sensor subsystem 80 further includes a second sensor unit 14 having a second sensing field 92 transversely directed toward travel path axis 44 and defining a second scanning zone 93, to generate second sensor output data related to the scanned board surface. In the presently described embodiment, the second sensor unit 14 is an optical, color image sensor unit, the generated second sensor output data representing board surface color-related characteristics including defects. It should be understood that although the operation of system 10 is less complex when the board are fed by conveyor 64 to the sensor subsystem 80 at a predetermined, substantially uniform speed along travel path axis 44, a predetermined, position/time profile could also be used. The speed or position/time profile operation of the system according to actual speed conditions can be performed by providing means for measuring the actual speed or position/time profile of the moving board, such as rotary encoders (not shown) coupled to entry conveyor 64 and to an exit conveyer 109 that will be described later, or any appropriate non-contact detectors (photocell arrays, laser velocimeter) disposed at proper locations within the sensor subsystem. The profile sensor unit 12 can conveniently use a same laser triangulation ranging approach as disclosed in U.S. Pat. No. 7,429,999 issued on the name of same assignee as of the present invention, in combination with a surface defect detection approach as the one disclosed in U.S. Pat.

No. 6,122,065 also issued to the same assignee, the whole content of which documents are being incorporated herein by reference. It is to be understood that sensor units 12, 14 which are optical in the context of the embodiment shown, may be of other types such as ultrasonic and X-rays, depending on the kind of characteristics to be detected and the nature of the articles being scanned. Moreover, even only first and second sensors units are involved in the shown embodiment, more than two sensor units may be integrated according to the approach of the present invention.

Figure 1C:
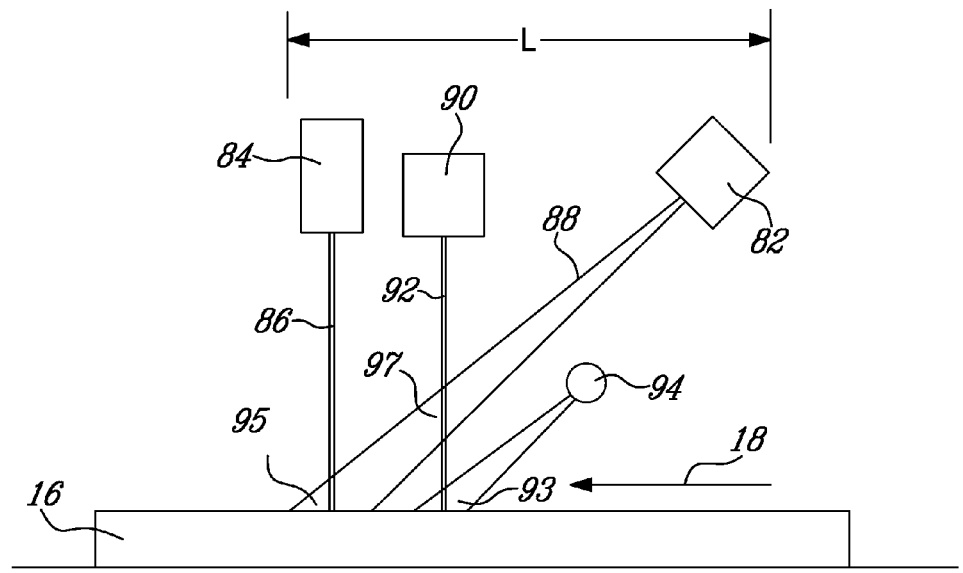
FIG. 1c is a schematic elevation view of the profile and image sensor units as part of the sensor subsystem showing the compact configuration thereof.
Figure 1D:
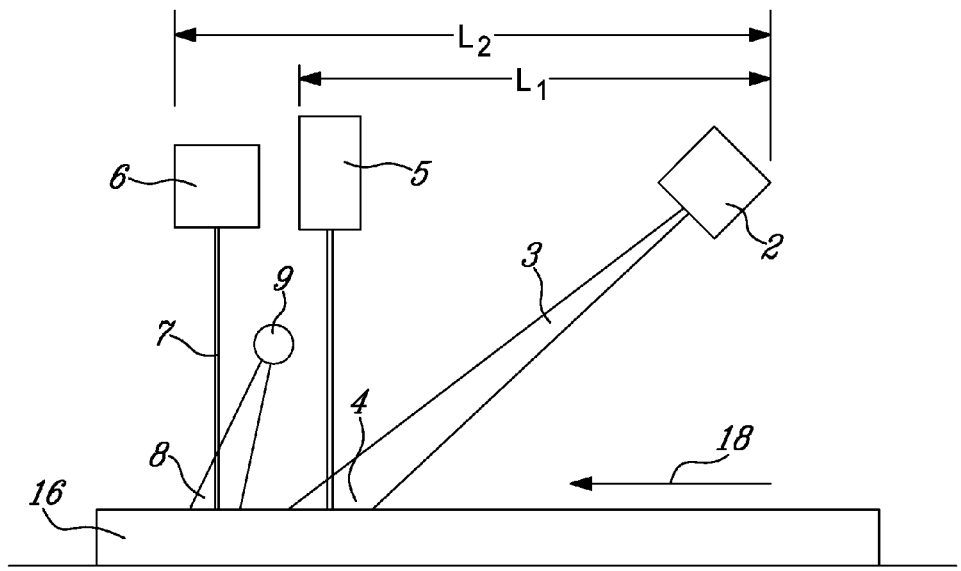
FIG. 1d is a schematic elevation view of a prior art configuration of sensor subsystem.

FIG. 1a shows the main components of the profile sensor unit 12, namely a first laser source 84 for directing a first, fan-shaped laser beam 86 toward first scanning zone 95 to form a first reflected laser line onto the scanned board surface, and a first digital matrix camera 82 defining first sensing field 88 and capturing a two-dimensional image of the first reflected laser line to generate corresponding two-dimensional image data. A 2352×1726 pixels matrix, high definition digital camera such as model A404K from Basler Vision Technologies (Germany), can be used. It can be appreciated in view of FIG. 1b that a board moving along the travel path axis 44 has its top surface intersecting sensing field 88' at a surface area onto which laser beam 86 reflect light toward camera 82. As shown in FIG. 1a, the color image sensor unit 14 provided on sensor subsystem 80 includes a first illumination source 94 in the form of fluorescent tubes for directing light toward the second scanning zone 93 to illuminate the scanned board surface, and a first digital color camera 90 defining second sensing field 92 and capturing an image of the illuminated board surface to generate corresponding color image data. It can be appreciated from FIG. 1c that first and second sensing fields 88, 92 are crossing one with another at a location generally designated at 97 sufficiently remote from first and second scanning zones 95, 93 so as to not adversely affect the generation of profile-related and color-related output data, while providing a compact arrangement of first and second optical sensor units 12, 14, as indicated by overall length L. In comparison with the prior art configuration of sensor subsystem such as shown in FIG. 1d, it can be appreciated that a more compact configuration is obtained. A linear, high definition digital color camera such as model Colibri 2048CL from TVI Vision Oy (Finland) can be used.

Although the inspection of only one article surface may be needed in some applications for the purpose of which the apparatus and method of the present invention may be used, inspection of first (top or bottom) and second (bottom or top) main surfaces of wooden boards is involved in the operation of the optimization system 10 as herein described. In this case, the first and second surfaces extending in substantially parallel spaced relationship, they can be simultaneously scanned using an appropriate sensor subsystem 80, wherein the first reflected laser line is formed onto first article surface, the profile sensor unit 12 has a third sensing field 88' transversely directed toward travel path axis 44 and defining a third scanning zone 95', and the color sensor unit 14 has a fourth sensing field 88' transversely directed toward travel path axis 44 and defining a fourth scanning zone 93'. More particularly, the profile sensor unit 12 further includes a second laser source 84' for directing a second, fan-shaped laser beam 86' toward third scanning zone 95' to form a second reflected laser line onto the second scanned board surface, and a second digital matrix camera 82' defining third sensing field 88' and capturing a two-dimensional image of the second reflected laser line to generate corresponding further two-dimensional image data. The pair of upper and lower high definition digital cameras 82, 82' are disposed in symmetrical relationship with respect to an image scanning plane that is aligned with the board conveying plane defined with respect to travel path axis 44 by the guiding and driving components of the sensor subsystem entry conveyor 64 as described above.

The color image sensor unit 14 provided on sensor subsystem 80 further includes a second illumination source 94' in the form of fluorescent tubes for directing light toward the fourth scanning zone 93' to illuminate the second scanned board surface, and a second digital color camera 90' defining fourth sensing field 92' and capturing an image of the illuminated board surface to generate corresponding further color image data. Here again, it can be appreciated from FIG. 1a that third and fourth sensing fields 88', 92' are crossing one with another at a location sufficiently remote from third and fourth scanning zones 95', 93' so as to not adversely affect the generation of profile-related and color-related output data, while still providing a compact arrangement of first and second optical sensor units 12, 14.

It can be seen from FIG. 1a that in the shown embodiment, the cameras 90, 90' are disposed with respect to the corresponding cameras 82, 82' so that a board moving along travel path 44 has its top and bottom surfaces intersecting, respectively at scanning zones 93 and 93', the sensing fields 92, 92' at a time prior to intersection of sensing fields 88, 88' by the same surface areas, respectively at scanning zones 95, 95'. The image illumination sources 94, 94' are preferably provided with cooling means (not shown) to provide temperature control. For a same purpose, each one of cameras 82, 82' and 90, 90' is also preferably provided with cooling means (not shown). In order to allow board thickness adjustment as mentioned before regarding sensor subsystem entry conveyor 64, an upper frame portion 100 of sensor subsystem 80 into which are adjustably secured upper cameras 82 and 90 with upper illumination source 94 is itself displaceably mounted on a lifting mechanism generally designated at 102 to selectively provide upward and downward movement of upper frame portion 100 with respect to main subsystem frame 104 according to the preset width characterizing the boards under processing. Prior to their operation, cameras 82, 82' and 90, 90' must be calibrated to ensure image sensing accuracy. Cameras 82, 82' of the profile sensor unit 12 can be calibrated according to the supplier specifications and using a calibration approach disclosed in the above-mentioned U.S. Pat. No. 7,429,999. As to the linear color cameras 90, 90' of the image sensor unit 14, they may be calibrated using any appropriate procedure involving reference charts of predetermined image intensity levels, such as black-white-grey or red-green-blue standard color components.

Turning back to FIG. 1, the sensor subsystem 80 is provided with a set of photoelectric cells 106, 107 for generating a signal whenever a leading edge of a board reaches respective entry ends of profile sensor unit 12 and image sensor unit 14 to generate a corresponding indicative signal to PLC 58. At a way out end of sensor subsystem 80 is disposed an exit conveyor 109 that is substantially a symmetrical version of the entry conveyor 64 described in detail above. The system exit conveyor 109 is also provided with an adjustable fence 111 that is associated with a further photoelectric cell 113 used to generate a fence positioning indicative signal to be sent to PLC 58. At a discharge end of the system exit conveyor 109 there is also provided a further photoelectric cell 115 to indicate through a corresponding electrical signal when the leading edge and trailing edge of a processed board sequentially leave the exit conveyor 109. Similarly to the entry conveyor 64, the exit conveyor 109 ensures board exit stability as well as speed regulation to a preset value or a predetermined, position/time profile. The exemplary system shown in FIG. 1 is further provided with a rotary loader 117 of a conventional design, whose function is to selectively direct a processed board toward a transfer catching chain conveyor 119. Sensor data generated by profile sensor unit 12 and image sensor unit 14 are sent through network bus 60 to at least one computer 125 provided at control centre 57 that is configured and programmed to perform sensor data acquisition and processing to obtain an optimized cutting solution for each scanned board. To enable an operator to remotely enter control parameter data and to monitor the system operation, a Keyboard-Video-Mouse switch (KVM) 201 is provided at control centre 57, which switch 201 is linked through communication line 123 to a local optimization system control station 126 that can be readily used by a local or remote operator to supervise and modify the operation parameters of the sensor subsystem 80 as well as of all conveyors 32, 64 and 109. The monitoring/control station 126 also enables the operator to proceed with camera calibration tasks. To each scanned board are associated optimization data that are stored into computer memory, which data are in turn associated with location data as will be later explained in detail. Also associated with sensor data corresponding to each scanned board is a board identification number that enables retrieval from the computer memory of data related to any specific scanned board 16 discharged by loader 117 onto the chain conveyor 119 for transporting the board 16 to an entry end of a marking station generally designated at 128. The marking station 128 includes an entry conveyor 130, a marking device 132 and an exit conveyor 134 which are respectively provided with board presence indicative photoelectric cells 129, 131 and 133 for respectively indicating the arrival of board 16 onto entry conveyor 130, its entry into marking station 132 and its discharge by exit conveyor 134. The marking device 132 is provided with a plurality of ink jet heads (not shown) that are disposed above the conveying plane of boards 16 as delimited by guiding fence 136, 137, respectively provided on entry and exit conveyors 130, 134. The operation of marking apparatus 132 is controlled by computer 125 through a communication line as part of network bus 60 by triggering selected ink jet heads according to optimized cutting layout data and taking account of the known board conveying speed in the direction of arrow 139 to produce unto the top surface of exiting board 16 a corresponding marking pattern 140 that can be viewed by an operator prior to physically subdivide the board accordingly. Furthermore, the marking station may apply onto the board its specific identification number and/or any section, subsection or part number that can be later used to retrieve data relevant to board cutting and/or part sorting operations. An automatic cross-cutting and ripping station (now shown) may be provided downstream the exit conveyer 134, to subdivide each board under process according specific part cutting layout data received from the production management station 61.

Figure 2:
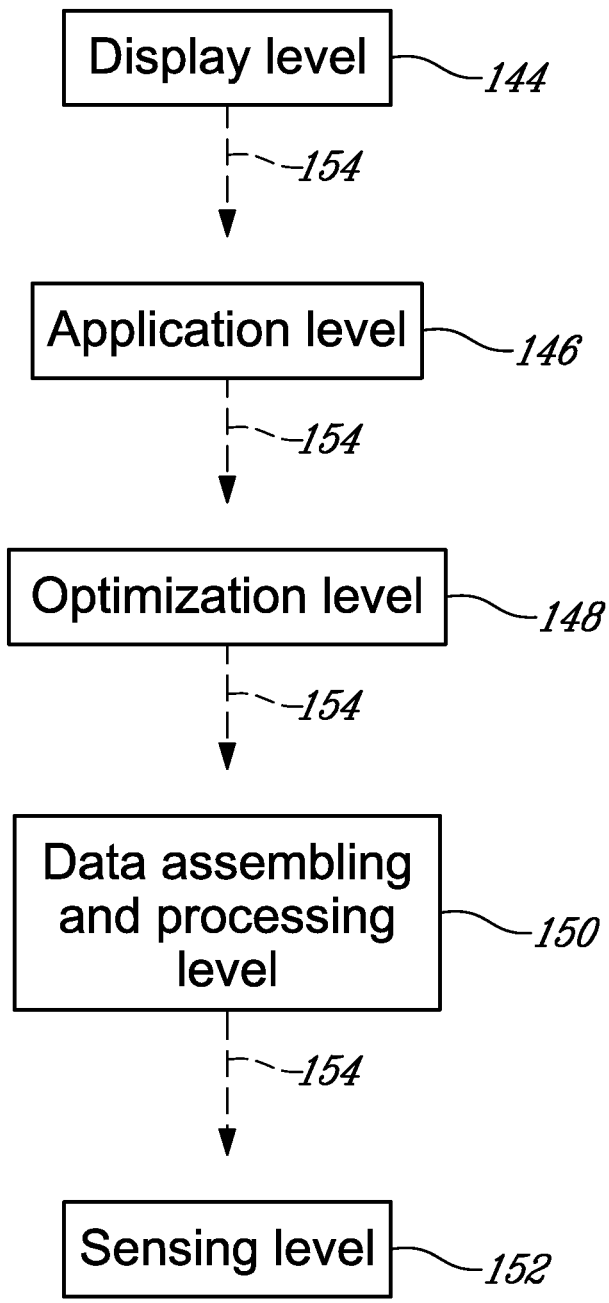
FIG. 2 is a block diagram showing the general hardware/software architecture of the optimization system physically represented in FIG. 1.

In view of FIGS. 2-12, a more detailed description of an example of the various hardware and software components that may be integrated in the optimization system generally described above will now be presented. Turning now to FIG. 2, the system architecture is conveniently divided in five hierarchical levels, namely display level 144, application level 146, optimization level 148, data assembling and processing level 150 and sensing level 152, wherein each hierarchically higher level is dependent upon hierarchically lower levels as indicated by arrows 154.

The display level 144 integrates all human-machine interfaces allowing a user to have access and modify information about the system. A first module provides access to information regarding parameter data related to the system such as quality grade editing data, optimization parameter editing data, as well as data on system assembly parameters and system calibration parameters. A second module allows access to information related to the control unit 58 referred to above in view of FIG. 1. Another module provides display and editing of information processed at parts production management station 61 as also referred to above in view of FIG. 1. Optionally, a further module allowing simulation of parts production management may be provided.

The application level 146 integrates software modules and specific data regarding operation of the system according to user's needs. A first, main controlling module is programmed to provide production start-stop coordination, data exchange between system components, command assignment to the optimizing modules, system database updating, data communication with control unit as well as other functions required to provide control over all data regarding the system. A second module allows the printing of cutting layout on the boards. It has the tasks of maintaining a waiting list for the cutting layouts of boards in current processing, and of synchronizing the detection of board identification with cutting layout printing. A third, database module provides storage of data related to system configuration, as well as data related to parts orders and production results. The database module has also the tasks of validating the data stored into the database, of performing data requests and of synchronizing competing data access. A programmable controller module integrated in PLC 58 provides tracking of boards through the optimization system, controlling of all conveyors provided on the system, as well as controlling mechanical driving of boards.

The optimization level 148 integrates the optimization and regulation algorithms enabling the system to estimate a best yield for an inspected board according to parts production orders. A first, optimizer module allows yield optimization for boards according to currently processed orders. It has the task of selecting the parts to include in a cutting layout so as to obtain a best yield for the produced parts according to the board characteristics, taking into account selected weighing factors for each part, as well as the task of updating stored data relating to currently processed parts orders. A second, regulator module provides regulation of boards and parts processing in/out rates for each parts order. It also has the task of modifying the weighing factors of the parts included in each order according to one or more regulating algorithms.

The data assembling and processing level 150 integrates all necessary functions to associate profile-related and color-related output data generated by each sensor unit with sensed location data for each scanned board surface as well as all processing functions aiming at standardization of board characteristics. A first, data assembling module provides sensed characteristics assembling in accordance with predetermined processing steps that will described later in more detail with reference to FIGS. 10-12, and has also the task of identifying false or incomplete association and to interrupt an assembling step when all characteristics-related data has not been received. A second, data processing module provides standardization of board characteristics through processing of assembled data and has the tasks of adjusting length and width of each board according to a predetermined rank of characteristics, of correcting the detected position of defects according to a common reference and of converting generated polygon-defining data into defect rectangle data.

The sensing level 152 integrates the functions performed by all various sensors provided in the system to obtain the desired board characteristics. A first, profile data processing module performs the measurement of profile, three-dimensional characteristics of each board, including surface defects such as holes, as well as dimensional measurements such as board thickness. It has also the tasks of two-dimensional image data digitizing, analyzing and profile detecting as well as transferring detected profile-related output data associated with each scanned surface to the communication network. A second, color data processing module provides color characteristic detection of the main surfaces of each board. It has the tasks of color image data digitizing, analyzing and color detecting, as well as of transferring color-related output data associated with each scanned surface to the data communication network 11. A third, knot data processing module provides detection of board surface characteristics associated with the presence of knots, and for so doing, has the tasks of image digitizing, analyzing and detecting surface knots area as well as of transferring the detected board surface characteristics-related data to the communication network.

Figure 3:
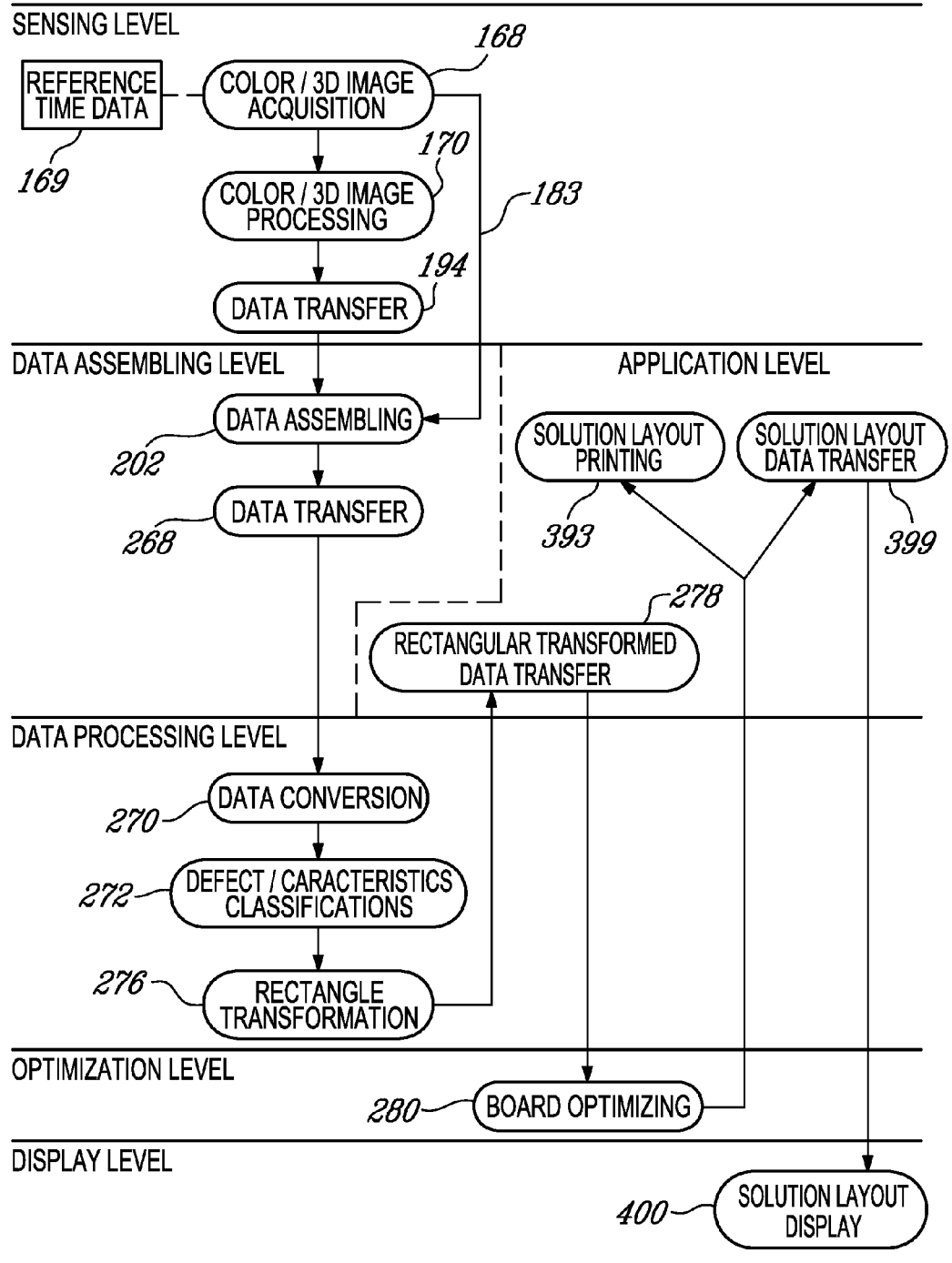
FIG. 3 is a flow chart showing the main steps performed at architecture levels shown in FIG. 2.

Referring now to FIG. 3, the various hardware and software components of the optimization system as described above in view of the physical schematic representation of FIG. 1, and according to the general hardware-software architecture as summarized above in view of FIG. 2, will now be described in more detail. Conveniently, the hardware/software components of board cutting optimization system 10 are based on a standard Object linking and embedding for Process Control (OPC) to provide modules and applications with access to the available data within a board cutting plant in a coherent manner. OPC allows hardware manufacturers to supply to system's developer software components providing data access from their own applications, without any need to program specific pilots for the supplied hardware. Details about OPC specifications can be obtained for OPC Foundation (Scottsdale, Ariz.). Furthermore, the Component Object Module (COM, Microsoft Corp.) architecture is conveniently used for module programming to allow integration of various software/hardware components available in the marketplace, COM being the basic architecture for high-level architecture such as OPC. COM architecture includes a binary standard definition to provide components compatibility, independence of programming languages, availability for various platforms (Microsoft Windows™, Apple McIntosh™, Unix™), a strong extensibility and evolution capability for modules and systems based on components. Furthermore, COM architecture provides efficient communication between components and computers within many processing tasks, memory sharing between components, errors management and dynamic loading of components. COM architecture is implemented using a COM server as an executable component capable of creating COM object, which COM server may be either a ".dll" (in process) or a ".exe" (out of process) file. Among other components, the COM architecture is used to develop sensor signal acquisition sub-systems, board characteristics analysis sub-systems, calibration sub-systems, optimizing modules, and regulating module. Furthermore, various software tools programmed using a high-level programming language such as C++ may be used to develop various further software components of the system, performing functions such as error management, patterns use (singleton, subject-observer) multi-task management, initialization file management, timestamp and delay management, network time synchronization management, container file management, data security management, operating system services, inter-tasks communication and mathematical computing. Although COM architecture may be conveniently used as a basis for modules and other components of the system, a dynamic link library (dll) architecture may also be used for a same purpose.

Figure 4:
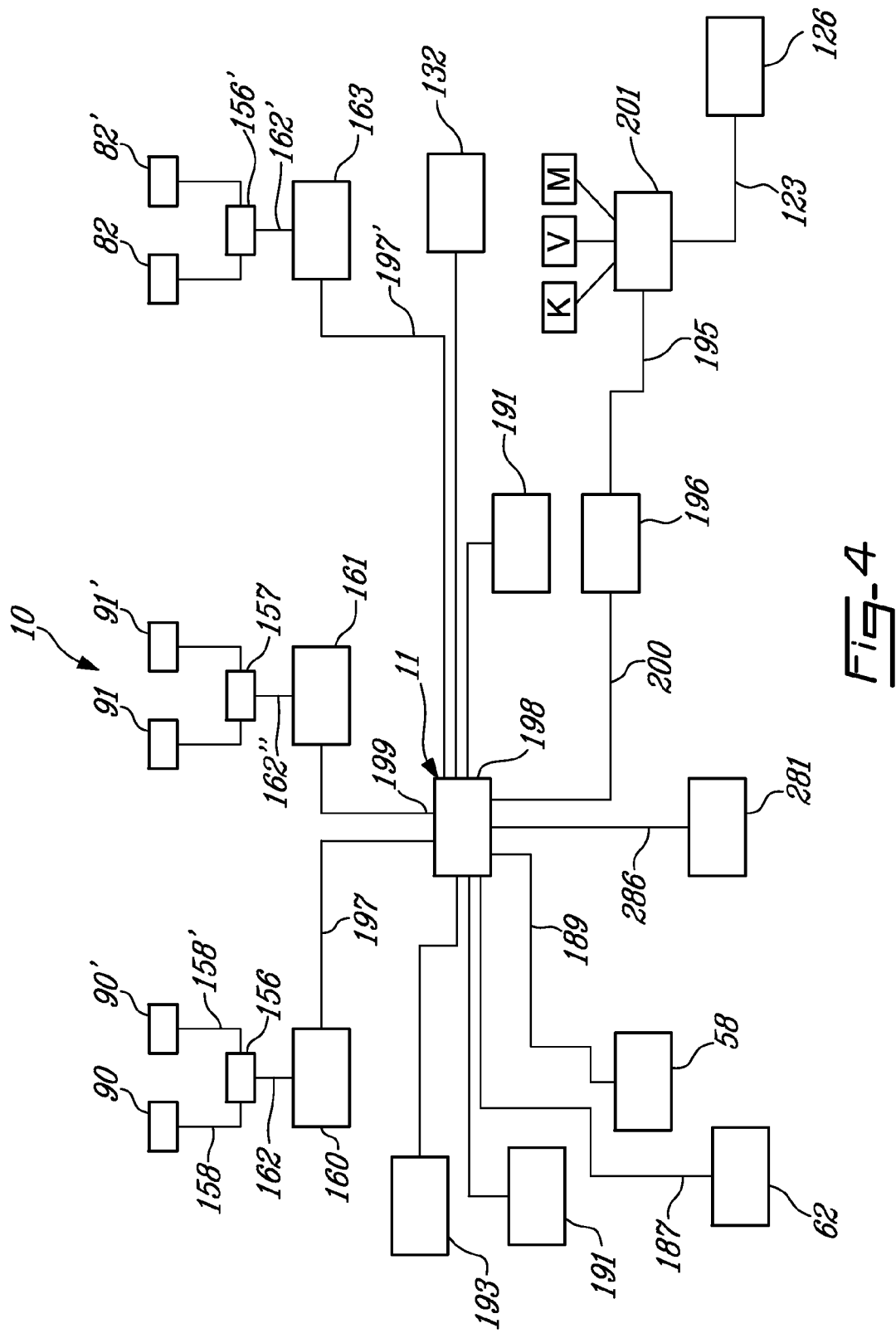
FIG. 4 is a structural block diagram showing in detail the various hardware and software components of the optimization system of FIG. 1.

Referring now to FIGS. 3 and 4, the imaging sensors functions and related components will now be described with respect to sensing, data assembling, data processing, optimization and display levels as introduced above, in term of data communication within these levels. At step 168 shown in FIG. 3, color imaging and three-dimensional imaging input data as generated by cameras 90, 90' and 82, 82' through pairs of lines 158, 158' and 159, 159' respectively, are acquired using image acquisition boards 156, 156', such as model Odyssey™ data acquisition boards from Matrox Electronic System Ltd (Dorval, Canada), respectively linked to a color data processing module 160 and a profile data processing module 163 through PCI-X buses 162, 162' as shown in FIG. 4. The invariant detection parameters such as design rules for camera files (DCF) and positioning of cameras can be modified from and stored in the computer of color data processing module 160. All parameters that can vary or may require an on-sight adjustment when the system is in operation are accessible via dialogue box provided by the interface of color data processing module 160. Since, in the present exemplary system, the boards to be inspected are fed to the system in a synchronous mode, image and profile data related to a predetermined number of inspected boards are stored in acquisition board memory until processing of said data is completed. It should be understood that an asynchronous mode of operation could also be applied. Typically, the number of inspected board is chosen at least equal to the number of available catching positions provided on the transfer conveyor 119 shown in FIG. 1, which directs the inspected boards toward marking station 128. As will be later explained in more detail, to allow assembling of color-related and profile-related output data with data representing sensed location on the moving inspected board, the data acquisition step 168 shown in FIG. 3 includes a local clock synchronization task involving a comparison with reference time data represented at block 169, for producing corresponding timestamp data used to update local time data accordingly. The updating time data is finally used to perform sensor output data assembling with corresponding sensed location data as indicated by arrow 183 directed to data assembling step indicated at block 202.

Figure 5:
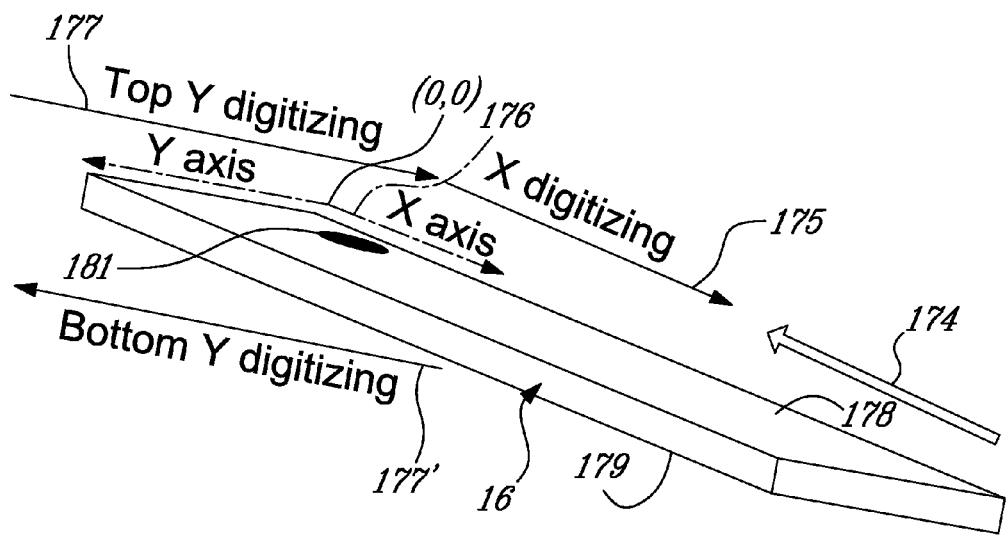
FIG. 5 is a schematic perspective view of a wooden board under scanning, showing the reference coordinates and directions for color image digitizing.
Figure 5A:
FIGS. 5a and 5b are raw color image representations of top and bottom surfaces of the wooden board of FIG. 5.
Figure 5B:
Figure 5C:
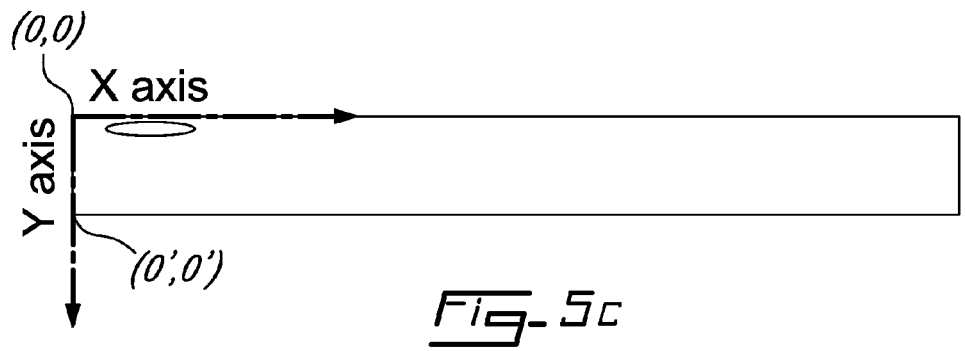
FIGS. 5c and 5d are realigned color image representations of top and bottom surfaces of the wooden board of FIG. 5.
Figure 5D:
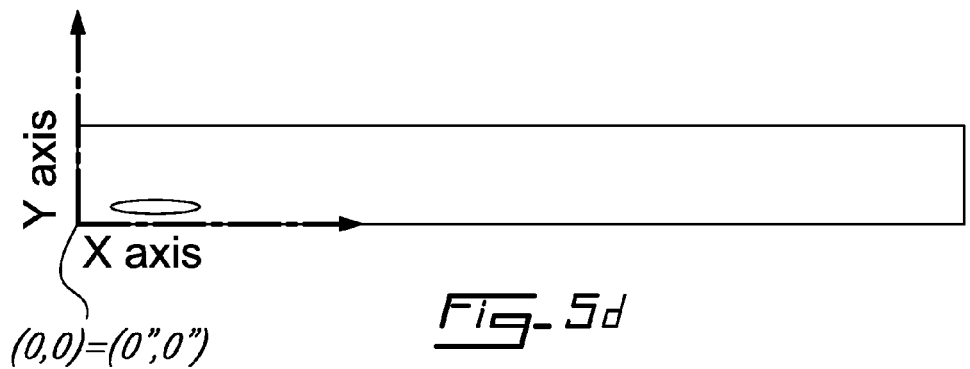

The manner according to which image data are produced through digitizing for purposes of color and knot sensing will now be explained in detail in view of FIGS. 5 and 5a-5d. Referring to FIG. 5, a wooden board 16 under scanning while passing through the sensor subsystem as described above in the direction of arrow 174 is depicted with respect to a reference system 176 defining x and y axis, whose origin coordinates (0, 0) correspond to board origin coordinates. The digitizing process along x axis is performed by the image sensor unit in the direction of arrow 175 for both top and bottom surfaces 178, 179 of board 16, while the digitizing process along y axis for board top and bottom surfaces is performed along directions of arrows 177 and 177', respectively. As to image resolution, since a linear camera is conveniently used by color data processing module 160, a one-dimensional CCD sensor array is involved and therefore, the scanned board is displaced perpendicularly with respect to the CCD array to form a two-dimensional image. While the resolution in the direction of the one-dimensional array is intrinsic to pixel density thereof, the resolution along the perpendicular direction will be determined by the relative distance traversed by the board between two successive image acquisition steps. For example, if the image acquisition rate is 1250 line/sec with a board moving at a speed of 55 m/min, a resolution between two consecutive acquired image lines of about 1 mm will be obtained. However, as well known in the art of image processing, a structure to be detected having its maximal dimension at the limit of a given sensor resolution may not be detected at a 100% rate, since a structure dimension that is at least twice the given sensor resolution would be required to achieve such rate, subjected to other external factors that might affect detection reliability in the context of a practical application. The raw color image representations of board top and bottom surfaces 178, 179 of FIG. 5 resulting from the digitizing processes are shown in FIGS. 5a and 5b, wherein it can be seen that origin coordinates (0, 0) of board top surface 178 do not correspond to image origin coordinates (0', 0') as shown at the bottom left corner of FIG. 5. Similarly, it can be seen from FIG. 5b that origin coordinates (0, 0) of board bottom surface 179 do not correspond to image origin coordinates (0", 0") as shown at the bottom left corner. It can further be seen from FIG. 5 in view of FIGS. 5a and 5b that a defect such as hole 181 extending throughout board 16 appears at the upper left corner of the image representation of FIG. 5a, while it appears at the lower left corner of the image representation of FIG. 5b. In order to simplify image data analyzing and processing, the raw color image representations are conveniently realigned with respect to the board origin coordinates (0, 0) as shown in FIGS. 5c and 5d, by translating the image origin coordinates (0', 0') of top surface 178 and image origin coordinates (0", 0") of board bottom surface 179 to the lower left corner of the board representation. It can further be seen from FIG. 5d that such translation makes bottom surface image origin coordinates (0", 0") to coincide with board origin coordinates (0,0). The resulting aligned color image data are then analyzed by the color data processing module 160 of FIG. 4 at processing step 170 shown in FIG. 3 to identify, locate and classify defects and other visual characteristics represented by polygon-defining data including cartesian coordinates in actual distance unit (usually in μm) with respect to the physical reference system used. An appropriate classifier can be readily developed by any person skilled in the art of computer programming, based on the teaching of known references such as Fukunaga "Introduction to statistical pattern recognition" Academic Press, 1990. An example of resulting analyzed image is given in FIG. 6, wherein a color-related defect is delimited by a large, 6-side polygon 184 and a slit is delimited by a small rectangle at 186. It can be also seen from FIG. 6 that outer perimeter 188 of board 16" can similarly be approximated by a polygon that is itself delimited within large rectangle 190 having its upper left corner coinciding with origin coordinates (0, 0) of the reference system defining x and y axes. Conveniently, each polygon-delimited area on board surface images can be displayed using a color specific to the type of defect or other characteristics so detected.

Figure 7:
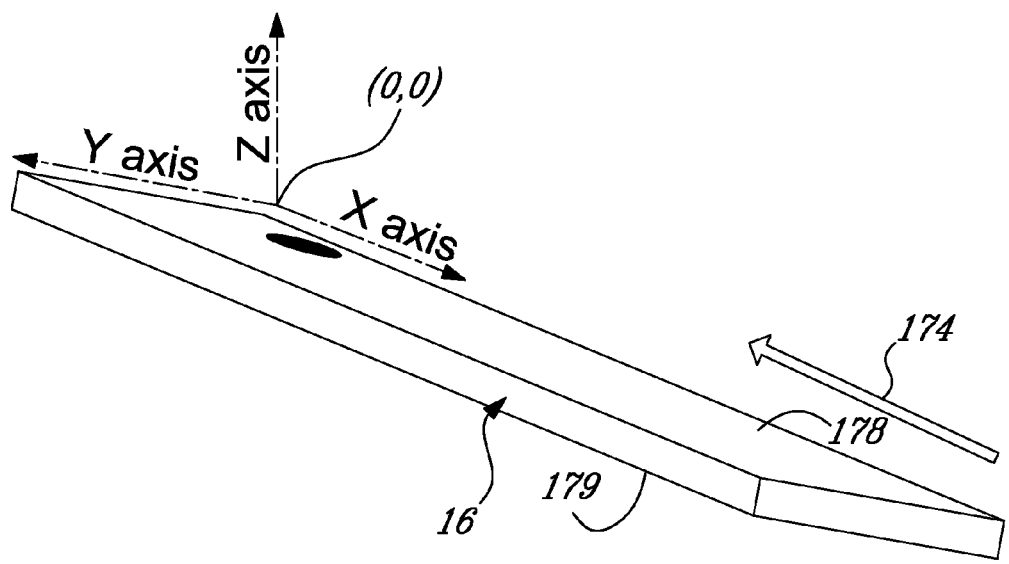
FIG. 7 is a schematic perspective view of the wooden board under scanning of FIG. 5, showing the reference coordinates and directions for 3D profile image digitizing.
Figure 7A:
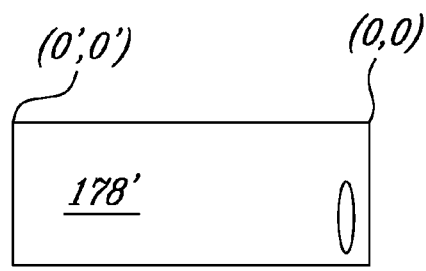
FIGS. 7a and 7b are raw image representations of top and bottom surfaces of the wooden board of FIG. 7 prior to profile derivation.
Figure 7B:
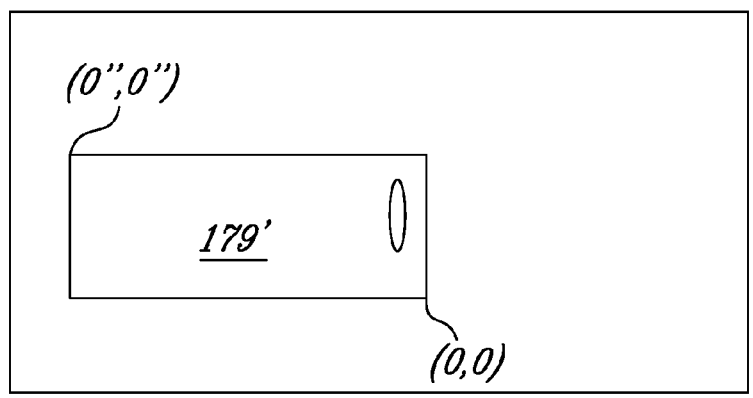

Referring now to FIG. 7, the same wooden board 16 as referred to above in view of FIG. 5 is now represented while being scanned by the profile sensor unit as described above, as board 16 passes therethrough in the direction of arrow 174, wherein the reference system shown defines, in addition to x and y axis, a third, z axis extending perpendicularly to the plane defined by x and y axes, to allow representation of 3-D profile data associated with both scanned surfaces 178 and 179 of board 16. It can be seen from FIG. 7 in view of FIG. 5 that the origin coordinates (0,0) are the same. The digitizing process performed by the profile sensor unit is similar than the one described above for the purpose of color image sensing, with the difference that it uses matrix digital cameras 82, 82' as shown in FIG. 4 and described in detail above in view of FIGS. 1a and 1b, so that a section 178' of top surface 178 and a section 179' of bottom surface 179 can be digitized in a single operation to give resulting raw image representations such as shown in FIGS. 7a and 7b for top and bottom surfaces, respectively. The resolution obtained with matrix digital cameras 82, 82' will depend upon the actual intersected area of the inspected surface board by the camera sensing fields 88, 88' as shown in FIGS. 1a and 1b as well as upon the intrinsic pixel density characterizing the CCD matrix array provided in cameras 82, 82'. For example, for a 40 cm×40 cm intersected area using a 2048×2048 CCD array, a resolution of about 0.2 mm×0.2 mm will be obtained. In practice, a maximum resolution of about 0.15 mm with respect to y axis as shown in FIG. 5, i.e. along transverse dimension of board 16, can be achieved, while a resolution along x axis also shown in FIG. 5, i.e. along lengthwise dimension of same board 16, may be achieved with high definition digital cameras available in the marketplace. It can be seen from FIGS. 7a and 7b that the location of origin coordinates (0, 0) for the raw profile image frame that covers surface section 178' is different than the location of the same origin coordinates (0, 0) with reference to the raw image frame that covers bottom surface section 179'. However, the camera origin coordinates (0', 0') with respect to top surface section 178' as shown in FIG. 7a is at the same location as camera origin coordinates (0", 0") associated with bottom surface section 179' as shown in FIG. 7b. In other words, for the top profile image as shown in FIG. 7a, the pixel associated with origin coordinates (0, 0) is located to the left of sensor subsystem entry conveyor 64 shown in FIG. 1 in the board feeding direction indicated by arrow 174, while for the bottom raw profile image, the pixel corresponding to origin coordinates (0, 0) is located to the same left side of conveyor 64 but seeing in a direction opposite from feeding direction indicated by arrow 174 shown in FIG. 7.

Figure 7C:
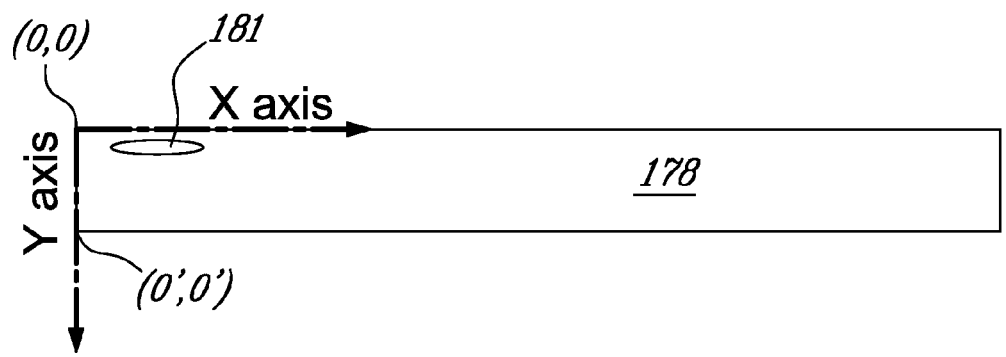
FIGS. 7c and 7d are resulting profile image representations of top and bottom surfaces of the wooden board of FIG. 7.
Figure 7D:
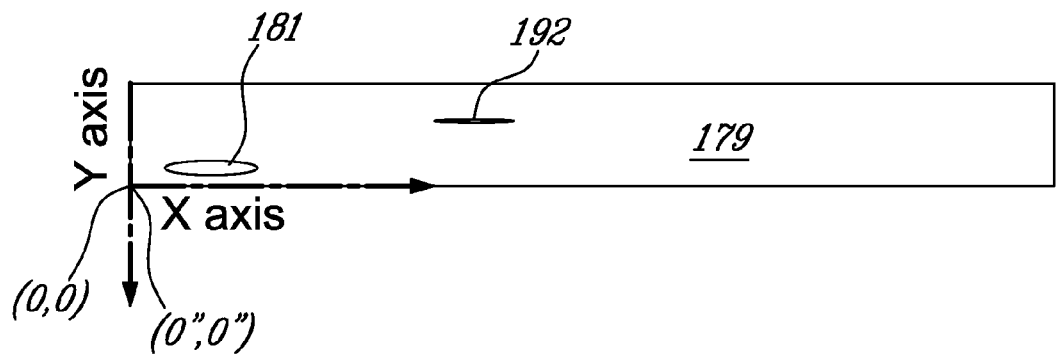

Referring now to FIGS. 7c and 7d, the resulting profile image representations of top and bottom surfaces 178, 179 are shown, wherein the values of z coordinates are conveniently indicated through various grey levels allowing the display of profile-characterized defect such as hole 181 visible on both top and bottom surfaces 178, 179 or split 192 only visible on bottom surface 179 and represented by a different grey level as compared with hole 181. Furthermore, a separate image representing thickness measurements derived through comparison of profile data characterizing top and bottom surfaces 178,179 may be built, wherein thickness variations can also be represented by a range of grey levels. In practice, a set of 256 grey intensity levels (0-256) generally provides an adequate mapping of z coordinates range as measured on typical pieces of lumber. It can be understood that both color-based characteristics and profile-based characteristics of a scanned board may be presented in a same displayed image by the graphical interface provided at the display level of the system. Three-dimensional image processing is also performed at step 170 as shown in FIG. 3, by the profile data processing module 163 of FIG. 4. For each face 178, 179 of board 16 as shown in FIG. 7, the profile data processing module 163 generates pixel centroid data for each column j of the CCD arrays provided on cameras 82, 82', which centroid data have been converted into "world" reference coordinates according to known TSAI transformation, as described in publication no. US2005/0270375 referred to above. Conveniently, in an analysis direct link library (dll), two representative images are created for each face 178, 179, the first being used to store y transversal indicative coordinates of centroids, the second being used to store z coordinates of same centroids. Then, thickness measurement is performed on the basis of found z image coordinates for each board face. As to bottom face 179, for each line i of z image coordinates, a linear regression is performed to generate a corresponding regression line. Then, for each point that has been used to build that line and perpendicularly thereto, the point nearest from that perpendicular direction is found within the representative images of y and z associated with top board surface 178. The difference between z coordinates found for that point within top face image and the z coordinates within the bottom face image gives the thickness measurement at that specific point. All thickness values so calculated form a further image representing thickness measurements for the whole board 16. Within that image representation, a point (i, j) gives a corresponding z coordinate, and each line i of that image represents a specific plane within the board, while each column j of that same image represents a camera CCD column, i.e. usually a y coordinate position on the same board. Conveniently, the z coordinates are defined with respect to the centre point of the calibration target that has been used in the calibration procedure preceding system operation. Since each coordinate j does not correspond to a constant, actual distance on board 16 with respect to y axis, the thickness representative image is corrected by converting each j coordinate with respect to a physical reference. For so doing, each point (i, j) in the thickness representative image is corrected using the y coordinates of bottom board face image in such a manner that point of coordinates (0,0) within the thickness representative image is associated with the physical origin coordinates of the board 16 with respect to sensor subsystem entry conveyor 64 shown in FIG. 1, and that each i within that same image is associated to a constant physical distance y on the board in transverse direction along y axis as shown in FIG. 7. Referring back to FIG. 3, the profile-related defect data are also transformed into polygon-defining data at processing step 170 for defining a delimited area around detected, profile-characterized defects.

Turning again to FIG. 4, optionally, as a complement to color sensing performed by module 160, there can be provided a knot data processing module 161 capable of identifying and locating that specific type of wood surface defect from either the same image data stored in board 156, or from further image data separately acquired by optional board 157 coming from optional cameras 91, 91' shown in FIG. 4. An appropriate classifier can also be readily developed by any person skilled in the field of computer vision to perform knot sensing, which can further be based on profile characteristics obtained from profile data processing module 163.

Upon operation of the system 10, the color, knot and profile data processing modules 160, 161 and 163 read, from respective acquisition board memory, sensed data that are associated with the first board, for transferring thereof to the image processing program generating a corresponding series of polygon defining coordinates data. Furthermore, data processing modules 160, 161 and 163 are capable of loading image files stored in the image acquisition board memory to insert thereof within currently processed board data stack. The modules 160, 161, 163 have the capability of storing raw, unprocessed image data fetched from acquisition board memory, and are further capable of loading processed data for displaying via their respective graphical interface, for diagnostic or other purposes. Although defects and other characteristics are classified as being either dimensional or visual in the exemplary system 10, such classification is conveniently based on the specific technology used by each data processing module. It should be understood that a particular defect or other characteristic that has been classified as visual since sensed by the color data processing module 160, could be classified into another category of defect or characteristic if an alternate sensing technology such as x-rays or microwave detector were used.

Turning back to FIG. 3, the polygon-defining data generated at processing step 170 is transferred at a following step 194 to the system main control module designated at 196 on FIG. 4 as part of the control centre 57 shown in FIG. 1 through LAN/OPC lines 197, 197', 199 and 200 connected to respective ports of a data switch module 198 linked to a UPS at 191 and to a SQL server station at 193 for allowing data access through the communication network generally designated at 11 in FIG. 4, which bears the same number in FIG. 1. As also shown in FIG. 4, also linked to communication network 11 are the local control/monitoring station 62 and PLC 58 through lines 187, 189, as part of network bus generally designated at 60 in FIG. 1. Optionally, data switch module 198 may be connected to the general communication network of the wood processing plant through an external data switch module at 191. As previously mentioned, to enable the operator to entry control parameter data and monitor operation the system, module 196 is connected to KVM switch 201 through control line 195 as shown in FIG. 4. The system main control module 196 is programmed to generate and store in memory all data received from data processing modules 160, 161 and 163, in the form of a file containing polygon-defining data with associated defect or other characteristic identification data, as well as dimensional data representing width (μm), length (μm), and actual surface (mm$^2$) of each respective board. At a step 202 in FIG. 3, at the data assembling level, the system control module 196 shown in FIG. 4 performs the task of assembling all sensed output data transferred thereto with corresponding data representing sensed location on inspected board 16. Each data acquisition module 156, 157 and 156' associated with data processing module 160, 161, 163 operating independently and in a synchronous mode, they can generate output data at any time following board scanning operation.

Figure 9:
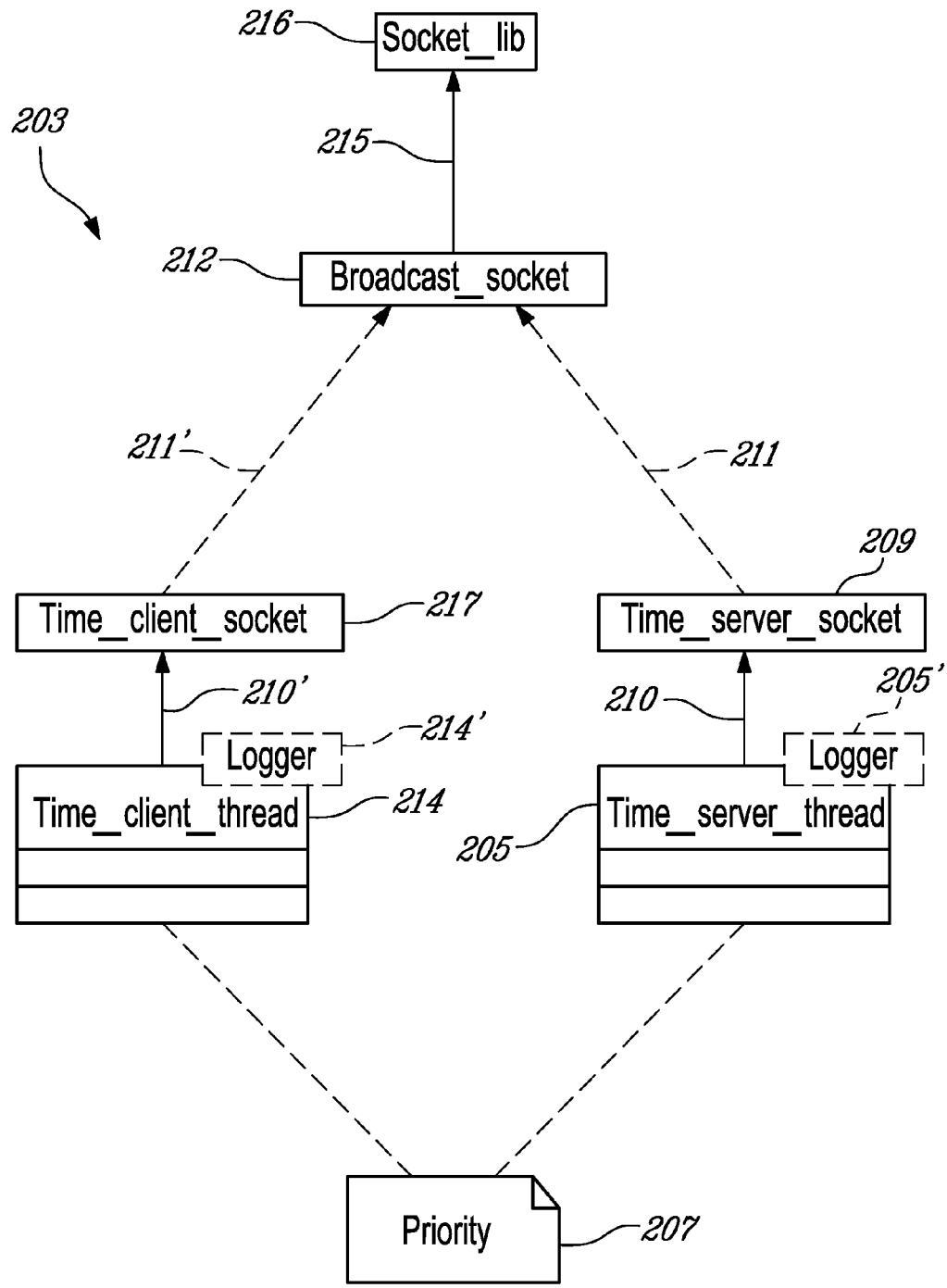
FIG. 9 is a block diagram showing the program object structure of an exemplary time socket that can be used by a computer software programmed according to the data assembling methods.

Referring now to FIG. 8, the proposed data assembling method will now be explained in detail in view of FIGS. 9 to 12. The method is used for assembling sensor output data such as polygon-defining data generated by either color, knot or profile modules 160, 161, 163 as described above in view of FIG. 4, with corresponding data representing sensor location on an article such as board 16 shown in FIGS. 5 and 7, moving at a known speed or position-time profile along the travel path in the direction of arrow 174 intersecting the sensing field associated with the sensor unit used, i.e. sensing fields of cameras 90, 90', 91, 91', 92 or 92' as shown in FIG. 4. Turning back to FIG. 8, the proposed data assembling method includes a first step 220 of transmitting reference time data through the data communication network 11 referred to above in view of FIG. 1 and FIG. 4. In the embodiment described herein, a socket is used as a basic tool to provide such data communication via a known TCP/IP transmission control and internet protocol using a user datagram protocol (UDP) frame in broadcast mode, in such a manner that any sensor module linked to the network 11 can receive such UDP frame through a time socket. In a case where the network 11 is a half-duplex local area network (LAN), all sensor units linked thereto receive a given UDP frame substantially at the same time, assuming that the LAN communication paths are substantially of a same length. Otherwise, knowing the delay induced by different travelling paths for transmitted data, a corresponding correction shall be applied to provide synchronization. The time socket used is linked to an assigned TCP port number to which data is transmitted. An example of time socket that can be used to transmit and receive UDP data frames on a TCP/IP network is shown by the diagram of FIG. 9, wherein the blocks represent object programs developed with a known high level programming language such as C$^{++}$. The global time socket generally designated at 203 includes an object named "time_server_thread" at 205, which is a server thread providing transmission of reference time data through the communication network according to the high rank priority given at 207. The server thread 205 is also associated with a logger 205' for registering the transmitted data. In operation, server thread 205 calls for, as indicated by arrow 210, an object named "time_server_socket" at 209, which in turn, as indicated by arrow 211, calls for an object named "broadcast_socket" enabling transmission in broadcast mode of a UDP data frame encoding the reference time data. The time socket 203 also includes an object named "time_client_thread" at 214, which client thread performs local clock updating through the communication network, according to the given high rank priority. The client thread 214 is also associated with a logger 214' for registering the transmitted data. In operation, client thread 214 calls for, as indicated by arrow 210', an object named "time_client_socket" at 217 for use by a client application, which in turn, as indicated by arrow 211', calls for "broadcast_socket" object 212 enabling the reception in broadcast mode of a UDP data frame encoding the reference time data. For so doing, object 212, as indicated by arrow 215, refers to "socket_lib" object 216 providing access to the main standard socket library of Microsoft Windows™ in the present example. It should be understood that another appropriate program architecture may be used to implement the time socket.

Figure 10:
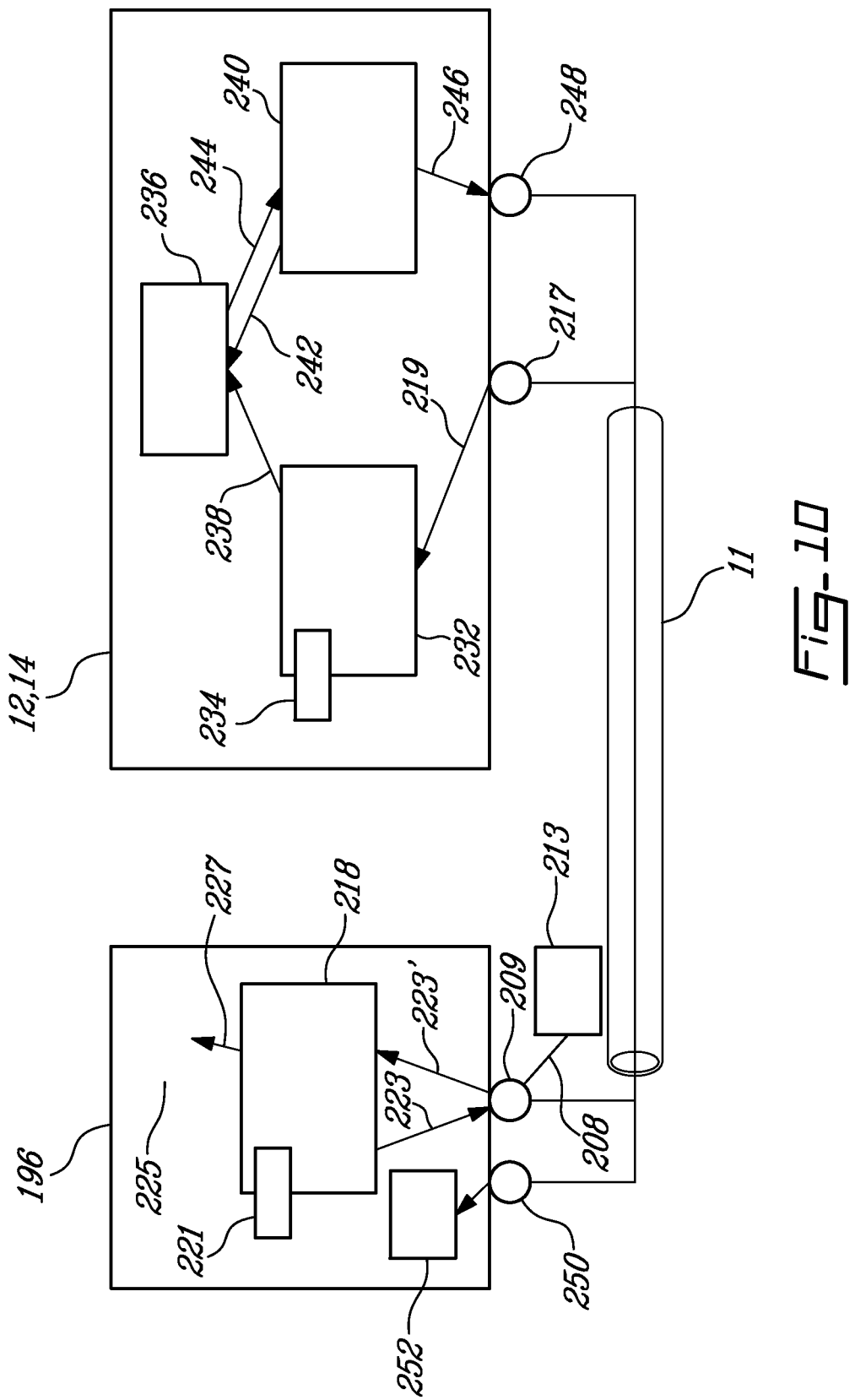
FIG. 10 is a block diagram schematically representing a first example of functional components linked to a data communication network using one of the data assembling methods.

Referring now to FIG. 10 representing a first example of functional components linked to internet communication network 11 and used to operate data assembling, the system main control module 196, as described before in view of FIG. 4, is now used in the instant example as a server computer having stored in memory for loading thereon, a time server program named "time_server.exe" represented at 218, and further having a high accuracy clock program 221 from which reference time data is obtained and directed to first time socket 209 as indicated by arrow 223. Conveniently, such high accuracy clock program 221 can be provided in the form a $C^{++}$ object using a high accuracy counter function provided on Microsoft Windows™ operating system named "Query Performance Counter" (QPC), allowing time synchronization as indicated by arrow 227 with a high frequency real-time clock (RTC) circuit 225 provided on the computer data processor included in main control module 196, which RTC circuit 225 can optionally be itself synchronized to an external timing reference of a higher level, if higher timing accuracy is desired. For so doing, a time data request can be generated by the time server program 218 and directed through time socket 209 and line 208 to an external server such as NTP or SNTP as designated at 213 on FIG. 10, which external server, having access to higher level timing data from a selected source such as GPS, CDMA or atomic clock, in turn sends back to the time server program 218 updated reference time data as indicated by arrow 223' to synchronize RTC 225 accordingly. Alternatively, a GPS unit may be directly linked to time socket 209 for the same purpose. When the time server program is launched according to high the priority indicators mentioned above, the time reference data is obtained using the server's RTC circuit 225 via a QPC request for updating the time server high accuracy clock. At regular time intervals or according to any other predetermined or arbitrary timeline, the current time reference data generated by the time server program 218 is transmitted through the communication network 11 via the first, server time socket 209 as also shown in FIG. 9, using a UDP frame and a TCP port as described above. The identification number of the TCP port used as well as the transmission timeline can be edited via an initialization file also loaded in the main control module 196, the path and file name thereof being stored in the operating system register. Following reference time data transmitting step 220 as shown in FIG. 8, the following sequence of steps 222, 224, 226, 228 and 230 are provided as part as the color and profile image data acquisition task represented at block 168 in the flow chart of FIG. 3. At step 222 shown in FIG. 8 and in view of FIG. 10, the reference time data transmitted through data communication network 11 is received via second time socket object 217 by a time client program 232 loaded on the computer provided on each sensor unit for which output data is required to be assembled with corresponding location data associated with the inspected board. It should be understood that while in the example shown in FIG. 10, each or both of profile and image sensor units 12, 14 can be provided with the time client program 232, further sensor units such as integrated knot data processing module 161 and associated acquisition board 157 and cameras 91, 91' can also be provided with time client program 232 for the same purpose. Furthermore, while the time client program 232 is conveniently loaded in the respective computer of data processing modules 160, 161 and 163 as shown in FIG. 4, it can alternatively be installed in respective image acquisition board 156, 157 and 156' receiving directly camera output data. In addition to the reference time data receiving function, the time client program 232 has also the task of comparing reference time data with local time data, at step 224 on the flow chart shown in FIG. 8, which is generated by a local clock substantially when the reference data is received at the corresponding sensor unit via second time socket object 217 as indicated by arrow 219.

In the example shown in FIG. 10, the local clock provided on sensor unit 12 or 14 integrates the accurate clock program using the accurate counter provided by the operating system as explained before and designated by block 234, and the real-time clock (RTC) at 236 provided on the data processing board integrated to the sensor unit computer. For so doing, the time client program has the capability of storing local time data provided by the high accuracy clock program 234 called for by time client program 232, which clock program 234 can be synchronized with the time server program whenever new time reference data is received depending on the result of the comparison made between the reference time data with current local time data generated by clock program 234 as stored by time client program 232. That comparison may be performed in several ways. A first comparison approach involves determining a difference between reference time data and local time data for then comparing the resulting difference with a limit value defining a predetermined range. In a case where that difference is found within such range, it can be assumed according to this approach that the corresponding time shift is caused by timing inaccuracies of clock program 234, and a time correction based on the earliest received time reference data is required accordingly. Alternatively, some other applications may be based on the assumption that when resulting difference is found within the predetermined range, a non-significant time shift on the part of the clock program 234 occurred, which does not require a correction on the basis of the received reference time data. Optionally, the program code can further include instructions for repetitively receiving successive time reference data transmitted through the data communication network 11 for comparison purpose with corresponding time data, and to count the number of times the estimated difference is successively outside the predetermined range. Then, whenever that number of times reaches a predetermined limit value, the program code initiates timestamp data generation even if the first condition explained above is not met, assuming that a timing problem involving the local clock may have occurred and that the reference time data is likely to be more accurate. Whenever a correction is required in accordance with the result of comparison step 224 in the chart of FIG. 8, the time client program shown in FIG.

10 produces timestamp data at a following step 226 in the chart of FIG. 8 and causes the local clock, via its clock program 234, to update its local time data according to the produced timestamp data. RTC circuit 236 is under synchronization control from clock program 234, in such a manner that the local clock is caused to update its local time data according to the received timestamp data, represented by step 228 in FIG. 8. Then, the RTC circuit 236 can be updated according to updated time data generated by clock program 234 via the time client program 232 as indicated by arrow 238. In turn, upon request of a sensor application program 240 involved in data acquisition and as indicated by arrow 242, the RTC circuit 236 transmits in turn updated time data to application program 240 as indicated by arrow 244 for associating updated time data with sensor output data upon generation thereof by corresponding sensor unit 12 or 14, as represented by step 230 in FIG. 8. The sensor output data with its associated updated time data can then be directed as indicated by arrow 246 to a third time socket 248, linked to a corresponding port of network 11, which time socket is conveniently opened through OPC or can be implemented according to a similar configuration as compared with time socket 217 as described above, to transmit these associated data through communication network 11. The associated data reach a fourth time socket 250 also linked to a corresponding port of network 11, which time socket 250 is then used by a data assembler program 252, loaded on the computer provided on the system main control module 196, and configured to assemble the sensor output data with the corresponding sensed location data according to the associated updated time data, as represented by step 202 in FIG. 8. For so doing, in view of the system 10 shown in FIG. 1, the known distances separating photoelectric cell 65 at sensor subsystem reference origin point on one hand and entry photoelectric cells 106, 107 respectively associated with profile and color sensor units 12, 14, on the other hand, allow the data assembler program to perform synchronization of data, on the basis of known board speed or position/time profile along the travel path indicated by arrow 18. In practice, upon starting of a board batch processing, start reference time data is stored in the main control module memory, and in a same manner, end reference time data is kept at the end of processing. To ensure system performance, a limit processing time condition can be imposed on the assembler program to complete assembling of the data generated by all sensors for a given location, and alarm data can be generated whenever processing time exceeds that limit.

Figure 11:
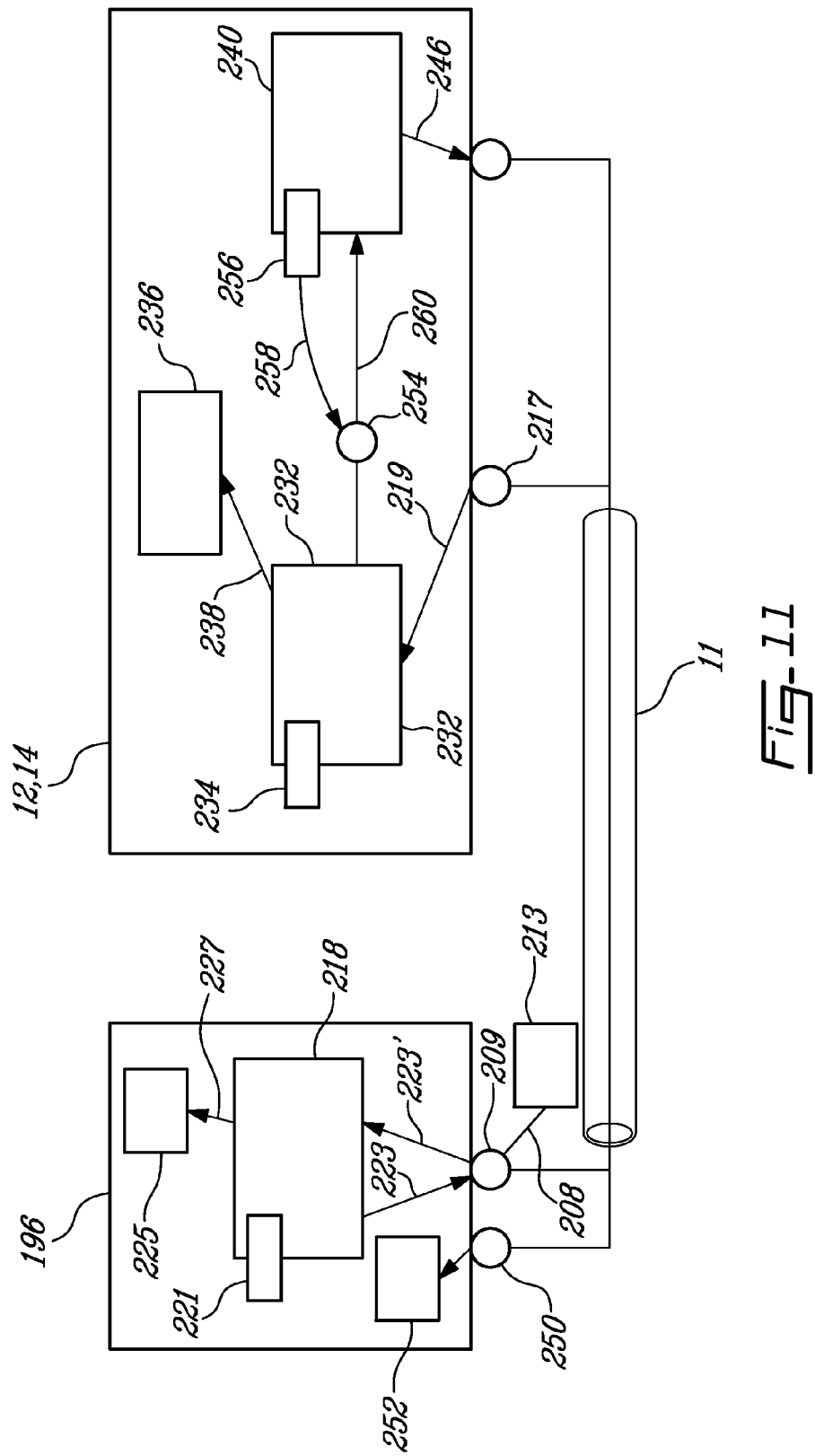
FIG. 11 is a block diagram schematically representing a second example of functional components linked to a data communication network using one of the data assembling methods.
Figure 12:
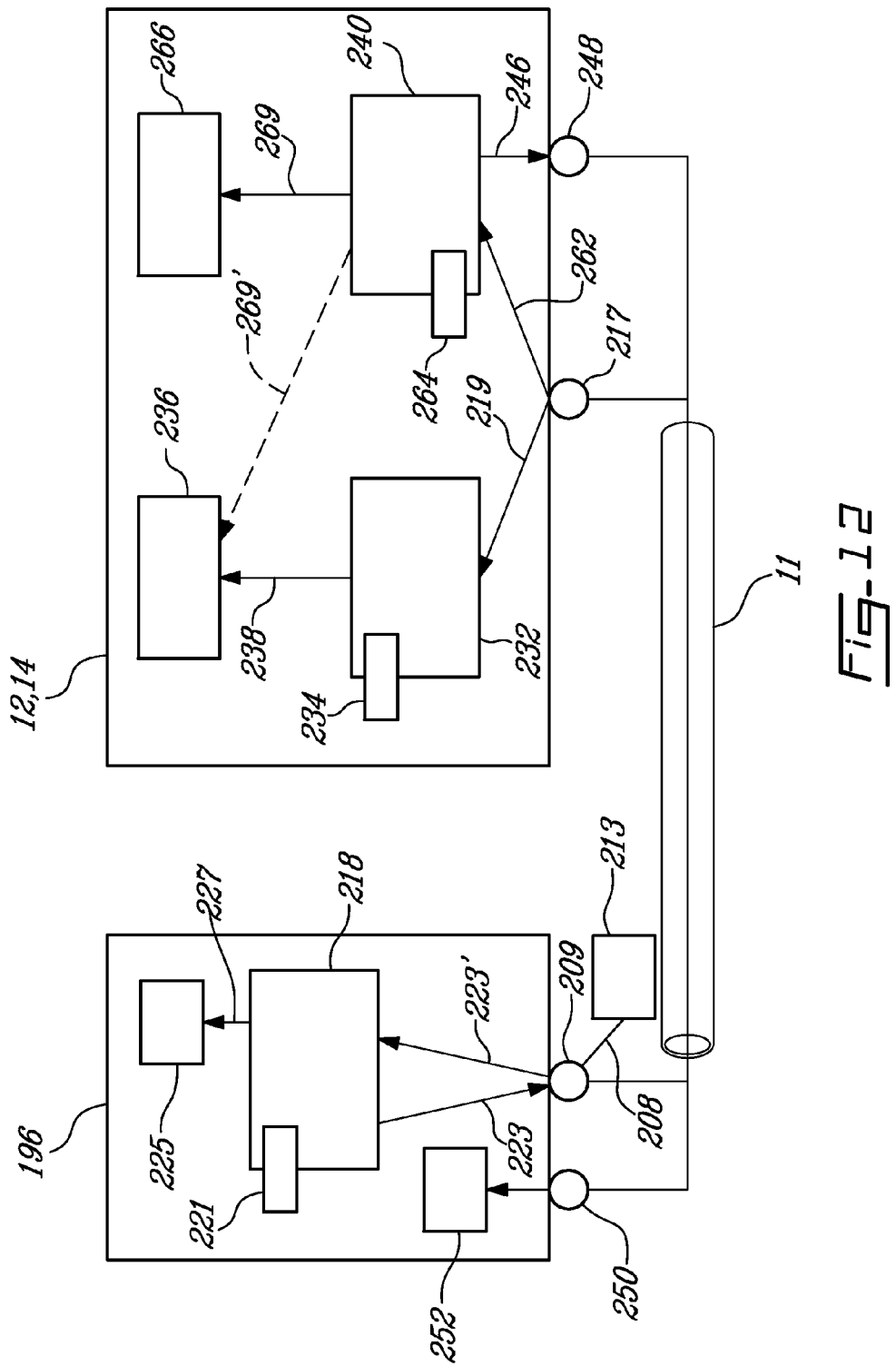
FIG. 12 is a block diagram schematically representing a third example of functional components linked to a data communication network using one of the data assembling methods.

Turning now to FIG. 11, there is shown a second example of functional components linked to data communication network 11 using another one of the proposed data assembling methods, which involves the same components as described above in view of the first example shown in FIG. 10, with an additional component designated at 254 representing an interface program adapted to communicate the update time data as it is generated by clock program 234, for enabling the sensor application program 240 to get updated time data as indicated by arrow 260, through time client program 232 and interface program 254 upon request as indicated by arrow 258, which is generated by routine 256 called for by sensor application program 240. In this case, rather than obtaining updated time data from RTC circuit 236, the sensor application program 240 makes more directly use of time server program 232 as a COM server via interface program 254, which can provide reference time data in various formats, such as universal time coordinated (UTC), from an external timing reference such as CDMA in FILETIME or SYSTEMTIME format, or from a local reference using SYSTEMTIME format. Although the use of an interface program 254 introduces a marshalling delay due to request processing, in cases where there is a limited number of time client applications having access to time client server 232, the configuration of FIG. 11 is likely to provide higher timing accuracy as compared with the configuration shown in FIG. 10. To obtain a still better accuracy, it is also possible to estimate the marshalling time for correcting the corresponding updated time data using a dividing "2" factor. In cases where still higher accuracy is desired, such for synchronizing low-level system components, the time socket 217 can be directly used by application program 240 as demonstrated in the example shown in FIG. 12. In this example, the sensor application program 240 is also adapted to receive reference time data from second time socket 217 as indicated by arrow 262, to compare thereof with local time data generated by high accuracy clock program 264 used as local clock for producing the timestamp data. The clock time program 264 associated with sensor application program 240 is caused to update local time data according to produced timestamp data. In this manner, a low level application program 266 also operating on the computer of sensor units 12, 14 can get accurate updated time data directly from sensor application program 240 as indicated by arrow 269, to synchronize its operation accordingly. Optionally, RTC circuit 236, rather than being under synchronization control from clock program 234 as indicated by arrow 238, can get updated time data directly from sensor application program 240 as indicated by arrow 269' shown in dotted line.

Figure 6:
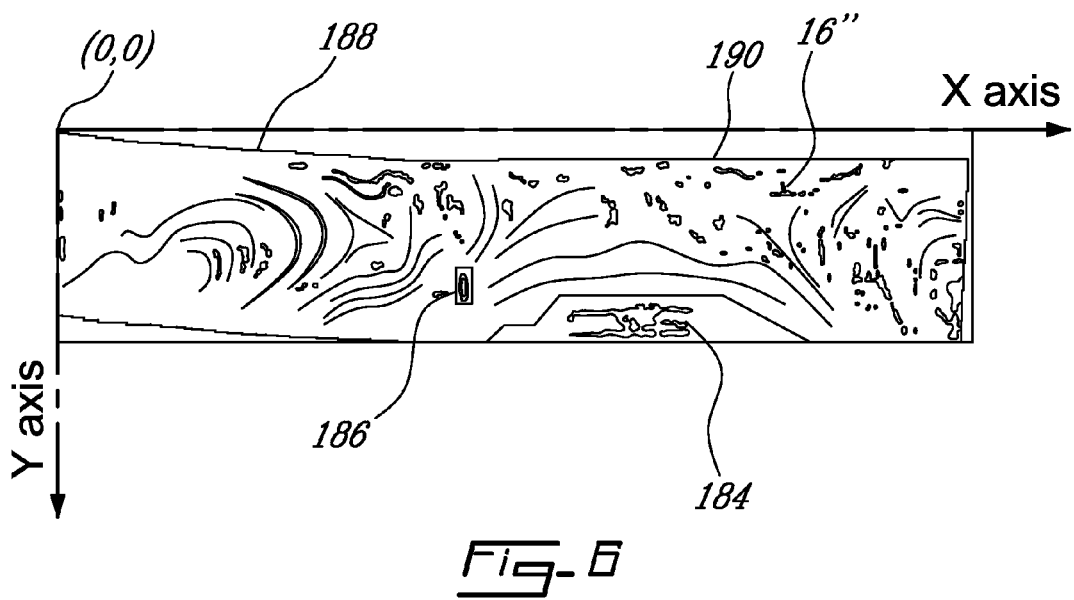
FIG. 6 is an example of an analysed image showing classified defect areas delimited by polygons.

Referring again to FIG. 3, at the data assembling level, the assembled data generated at step 202 is transferred through a following step 268 as part of data processing level, to a conversion step 270 providing standardization of board characteristics by adjusting length and width of each inspected board and correction of detected defect positions according to a common reference, as explained above in view of FIG. 2. Such post-detection processing is required since board characteristics data as obtained from various sensors each being of a distinct nature and characterized by different specifications, such as sensing resolution and measurement reference system. Then, converted polygon-defining data associated to the sensed defects and other characteristics of the inspected board are classified at step 272 on the basis of predetermined grading parameters. Configuration data defining each grade are stored in memory by the system main control module 196 as shown in FIG. 4 and can be modified as desired by the operator prior to starting the optimization process on the basis of an updated list of grades. Following the assignment of grade data to the converted polygon-defining data corresponding to the sensed characteristics, the latter is subjected to a transformation into rectangular characteristic defining data at step 276, in the form of coordinates list and location data that will be used at a later optimization step to produce the layout of selected part to be cut with respect to first (x) and second (y) orthogonal reference axes as shown in FIG. 6. The rectangular transformed data are then stored in memory by the system main control module 196 shown in FIG. 4, which in turn transfers these data at step 278 as part of the application level as shown in FIG. 3, to an optimizer module designated at 281 in FIG. 4, via line 200 and through data switch module 198 and LAN/OPC communication lines 286, the optimizer 281 performing board optimizing as indicated at step 280 in FIG. 3 as part of the optimization level of the system architecture shown. Then, at step 393, the data defining the solution layout are sent to the marking station 132 as shown in FIGS. 1 and 4, and is also transferred at step 399 for displaying at following step 400, through the displaying interfaces provided on local control station 126, system main control module 196 and part production management station 61 shown in FIG. 1.

Although an optimization method such as disclosed in U.S. Pat. No. 6,690,990 may be implemented to carry out board optimizing task, it should be understood that any appropriate alternative method of optimizing the layout of selected parts to be cut is contemplated. Moreover, while the application example of the data assembling method according to the invention as described above relates to lumber processing, it should be understood that the proposed method can also be advantageously employed in other industrial contexts, whenever sensor output data have to be assembled with data representing sensed location on an article moving at a known speed or position/time profile.

We claim:

1. An apparatus for scanning at least one surface of an article moving along a travel path axis, comprising:
    a profile sensor unit having a first sensing field transversely directed toward said travel path axis and defining a first scanning zone, to generate profile-related sensor output data related to said article surface;
    a color image sensor unit having a second sensing field transversely directed toward said travel path axis and defining a second scanning zone, to generate color-related sensor output data related to said article surface;
    wherein said first and second sensing fields are crossing one with another at a location sufficiently remote from said first and second scanning zones so as to not adversely affect the generation of said profile-related and color related sensor output data, while providing a compact arrangement of said profile and color image sensor units.

2. The apparatus according to claim 1, wherein said article is moving at known speed or position/time profile along said travel path axis, said apparatus further comprising data processing means for assembling said profile-related and color-related sensor output data with corresponding data representing sensed location on said article surface.

3. The apparatus according to claim 2, further comprising:
    a data communication network linked to said profile and color image sensor units;
    a server linked to said data communication network for transmitting reference time data therethrough;
    each one of said profile and color image optical sensor units having a local clock and being adapted to receive said reference time data, to compare said reference time data with local time data generated by said local clock substantially when said reference time data is received, to produce timestamp data in accordance with a result of the comparison, to cause said local clock to update its local time data according to said timestamp data, to associate updated time data generated by said local clock with respective said profile-related and color-related sensor output data upon generation thereof, and to transmit through the communication network respective said profile and color image sensor output data and respective updated time data associated therewith; and
    a data assembler linked to said communication network for assembling said profile-related and color-related sensor output data with the corresponding sensed location data according to respective said associated updated time data.

4. The apparatus of claim 3, wherein said server is provided with a time server program adapted to transmit said reference time data, each said profile and color-related sensor units being provided with a time client program adapted to receive said reference time data.

5. The apparatus of claim 3, wherein said time client program is further adapted to perform said comparison.

6. The apparatus of claim 5, wherein said time client program is further adapted to produce said timestamp data.

7. The apparatus of claim 6, wherein said local clock comprises a clock program associated with said time client program and caused to update said local time data according to said timestamp data.

8. The apparatus of claim 7, wherein each one of said profile and color image sensor units is further provided with:
    a sensor application program adapted to perform the association of respective said profile-related and color-related sensor output data with respective said updated time data; and
    an interface program adapted to communicate said updated time data as generated by said clock program to the sensor application program.

9. The apparatus of claim 6, wherein said local clock comprises a clock program associated with said time client program and a real time clock circuit under synchronization control from said clock program to be caused to update said local time data according to said timestamp data.

10. The apparatus of claim 3, wherein said communication network comprises:
    a first time socket used by said server to transmit the reference time data through said data communication network;
    a second time socket used by each one of said profile and color image sensor units to receive said reference time data;
    a third socket used by each one of said profile and color image sensor units to transmit respective said profile-related and color-related sensor output data with respective said updated time data associated therewith; and
    a fourth socket used by said data assembler to receive said profile-related and color-related sensor output data with respective said updated time data associated therewith.

11. The apparatus of claim 10, wherein each one of said profile and color image sensor units is provided with a sensor application program adapted to receive respective said reference time data, to perform said comparison, to produce said timestamp data and to perform the association of respective said updated time data with respective said profile-related and color-related sensor output data, wherein said local clock comprises a clock program associated with said sensor application program and caused to update said local time data according to said timestamp data.

12. The apparatus according to claim 1, wherein said profile sensor unit includes: a first laser source for directing a first laser beam toward said first scanning zone to form a first reflected laser line onto said article surface;
    a first digital matrix camera defining said first sensing field and capturing a two-dimensional image of said first reflected laser line to generate corresponding two-dimensional image data; and
    data processing means for deriving said profile-related output data from said corresponding two-dimensional image data.

13. The apparatus according to claim 1, wherein said color image sensor unit includes:
    a first illumination source for directing light toward said second scanning zone to illuminate said article surface;

a first digital color camera defining said second sensing field and capturing an image of said illuminated article surface to generate corresponding color image data; and data processing means for deriving said color-related output data from said color image data.

14. The apparatus according to claim 13, wherein said article has at least first and second surfaces extending in substantially parallel spaced relationship and being scanned, said first reflected laser line being formed onto said first article surface, said profile-related output data including profile-related output data associated with said first surface, said color-related output data including color-related output data associated with said first surface, said profile sensor unit having a third sensing field transversely directed toward said travel path axis and defining a third scanning zone, said color sensor unit having a fourth sensing field transversely directed toward said travel path axis and defining a fourth scanning zone;

wherein said profile sensor unit further includes:
a second laser source for directing a second laser beam toward said third scanning zone to form a reflected laser line onto said second article surface;
a second digital matrix camera defining said third sensing field and capturing a two-dimensional image of said second reflected laser line to generate corresponding further two-dimensional image data;
data processing means for deriving further profile-related output data associated with said second surface from said further two-dimensional image data; and
wherein said color image sensor unit further includes:
a second illumination source for directing light toward said fourth scanning zone to illuminate said second article surface;
a second digital color camera defining said fourth sensing field and capturing an image of said illuminated second article surface to generate corresponding further color image data;
data processing means for deriving further color-related output data associated with said second article surface from said further color image data; and
wherein said third and fourth sensing fields are crossing one with another at a location sufficiently remote from said third and fourth scanning zone so as to not adversely affect the generation of said further profile-related and color-related output data, while providing a compact arrangement of said profile and color image sensor units.

15. The apparatus according to claim 14, wherein said article is moving at known speed or position/time profile along said travel path axis, said apparatus further comprising data processing means for assembling all said profile-related and color-related output data with corresponding data representing sensed location on said first and second article surfaces.

16. A method for scanning at least one surface of an article moving along a travel path axis, comprising:
i) transversely directing a first sensing field of a profile sensor unit toward said travel path axis, said first sensing field defining a first scanning zone, to generate profile-related sensor output data related to said article surface; and
ii) transversely directing a second sensing field of a color image sensor unit toward said travel path axis, said second sensing field defining a second scanning zone, to generate color-related sensor output data related to said article surface;

wherein said first and second sensing fields are crossing one with another at a location sufficiently remote from said first and second scanning zones so as to not adversely affect the generation of said profile-related and color-related sensor output data, while providing a compact arrangement of said first and second sensor units.

17. The method according to claim 16, wherein said article is moving at known speed or position/time profile along said travel path axis, said method further comprising a step of:
iii) assembling said profile-related and color-related sensor output data with corresponding data representing sensed location on said article surface.

18. The method according to claim 17, wherein each said profile and color image optical sensor unit has a local clock and is linked to a data communication network, said assembling step iii), for each said profile-related and color-related sensor output data, including the steps of:
i) transmitting reference time data through said data communication network;
ii) receiving said reference time data at said sensor unit;
iii) comparing said reference time data with local time data generated by said local clock substantially when said reference time data is received at said step ii)
iv) producing timestamp data in accordance with a result of said step iii);
v) causing said local clock to update its local time data according to said timestamp data;
vi) associating updated time data generated by said local clock with said sensor output data upon generation thereof; and
vii) assembling said sensor output data with the corresponding sensed location data according to said associated updated time data.

19. The method according to claim 18, wherein said step i) is performed by a time server program linked to said data communication network, each said sensor unit being provided with a time client program adapted to perform said step ii).

20. The method of claim 19, wherein said time client program is further adapted to perform said step iii).

21. The method of claim 20, wherein said time client program is further adapted to perform said step iv).

22. The method of claim 21, wherein said time client program is further adapted to perform said step v).

23. The method of claim 22, wherein said local clock comprises a clock program associated with said time client program and caused to update said local time data according to said timestamp data.

24. The method of claim 23, wherein said step vi) is performed by a sensor application program provided on each said sensor unit, and there is provided an interface program adapted to communicate said updated time data as generated by said clock program to the sensor application program.

25. The method of claim 22, wherein said local clock comprises a clock program associated with said time client program and a real time clock circuit under synchronization control from said clock program to be caused to update said local time data according to said timestamp data.

26. The method of claim 19, wherein said step vii) is performed by a data assembling program linked to said data communication network, said method further comprising, between said steps vi) and vii), the steps of:
a) transmitting said sensor output data with said associated updated time data through said data communication network; and
b) causing said data assembling program to receive said sensor output data with said associated updated time data.

27. The method of claim 26, wherein said communication network is provided with:
- a first time socket used by said time server program to transmit said reference time data through said data communication network;
- a second time socket for use when receiving the reference time data at said sensor unit;
- a third socket used to transmit said sensor output data with said associated updated time data; and
- a fourth socket used by said data assembling program to receive the sensor output data with the associated updated time data.

28. The method of claim 19, wherein said communication network is provided with:
- a first time socket used by said time server program to transmit said reference time data through said data communication network; and
- a second time socket for use when receiving the reference time data at said sensor unit.

29. The method of claim 18, wherein each said sensor unit is provided with a sensor application program adapted to perform said steps ii), iii), iv), v) and vi);
- wherein said local clock comprises a clock program associated with said sensor application program and caused to update said local time data according to said timestamp data.

* * * * *